United States Patent [19]
Wick et al.

[11] Patent Number: 5,679,373
[45] Date of Patent: Oct. 21, 1997

[54] PROCESS OF ASSEMBLING A TRANSDERMAL PATCH INCORPORATING A POLYMER FILM INCORPORATED WITH AN ACTIVE AGENT

[75] Inventors: John Wick, Essex Junction; Ludwig J. Weimann, Burlington, both of Vt.; Wayne C. Pollock, Riverton, N.J.

[73] Assignee: Bertek, Inc., St. Albans, Vt.

[21] Appl. No.: 477,042

[22] Filed: Jun. 7, 1995

Related U.S. Application Data

[62] Division of Ser. No. 426,492, Apr. 20, 1995, which is a continuation of Ser. No. 861,534, Apr. 1, 1992, abandoned.

[51] Int. Cl.$^6$ .................................................. A61F 13/02
[52] U.S. Cl. ........................ 424/448; 424/449; 427/2.31
[58] Field of Search .............................. 424/448, 449; 427/2.31

[56] References Cited

U.S. PATENT DOCUMENTS

| | | | |
|---|---|---|---|
| 4,710,191 | 12/1987 | Kwiatek et al. | 424/449 |
| 4,839,174 | 6/1989 | Baker et al. | 424/447 |
| 4,840,796 | 6/1989 | Sweet et al. | 424/448 |
| 4,908,213 | 3/1990 | Govil et al. | 424/447 |
| 4,943,435 | 7/1990 | Baker et al. | 424/448 |
| 5,006,342 | 4/1991 | Cleary et al. | 424/445 |
| 5,023,084 | 6/1991 | Chien et al. | 424/448 |
| 5,126,144 | 6/1992 | Jaeger et al. | 424/448 |

FOREIGN PATENT DOCUMENTS

| | | |
|---|---|---|
| 0 338 819 | 10/1989 | European Pat. Off. . |
| 2184016 | 6/1987 | United Kingdom . |

*Primary Examiner*—D. Gabrielle Phelan
*Attorney, Agent, or Firm*—Lerner, David, Littenberg, Krumholz & Mentlik

[57] ABSTRACT

Devices for the controlled release of an active agent to the skin or mucosa of a host are disclosed, which devices are laminates of a backing layer, a monolithic carrier layer of an active ingredient selected from active agent, active agent enhancers and mixtures thereof, melt-blended with a thermoplastic matrix polymer capable of controllably releasing the active ingredient, wherein the active ingredient is heat stable at the melt temperature of the matrix polymer, together with means for affixing the laminate to the skin or mucosa of the host so that the active ingredient is continuously released from the carrier layer thereto. Methods for assembling the device are also disclosed, in which a thermoplastic matrix polymer capable of controllably releasing an active ingredient is melt-blended with an active ingredient that is heat stable at the melt temperature of the matrix polymer, so that a melt-blend of the active ingredient and the thermoplastic matrix polymer is formed, which melt-blend is formed into a monolithic carrier layer, and the carrier layer is then combined with a backing layer and means for affixing the laminate to the skin or mucosa of the host so that the active ingredient is released from the carrier layer thereto.

44 Claims, 7 Drawing Sheets

PROCESS OF ASSEMBLING A TRANSDERMAL PATCH INCORPORATING A POLYMER FILM INCORPORATED WITH AN ACTIVE AGENT

This is a division of application Ser. No. 08/426,492, pending, filed on Apr. 20, 1995, which is a File Wrapper Continuation of prior application Ser. No. 07/861,534, filed on Apr. 1, 1992, now abandoned.

BACKGROUND OF THE INVENTION

The present invention relates to a device for the controlled release of an active agent to a host. In particular, the present invention relates to a transdermal delivery patch having a monolithic polymeric carrier layer into which the active agent is melt-blended. More particularly, the present invention relates to transdermal devices for the topical application of active agents such as nicotine.

Transdermal administration systems are well-known in the art. Occlusive transdermal patches for the administration of an active agent to the skin or mucosa are described in U.S. Pat. Nos. 4,573,996 4,597,961 and 4,839,174.

One type of transdermal patch is a polymer matrix or monolithic device in which the active agent is dissolved or suspended in a polymer matrix film through which the active agent diffuses to the skin. Such patches are preferred because they are relatively simpler to manufacture compared to reservoir-type devices. Transdermal patches having a monolithic polymer film layer into which the active agent is dissolved or suspended are disclosed by the above-mentioned U.S. Pat. No. 4,839,174, as well as by U.S. Pat. Nos. 4,908,213 and 4,943,435.

U.S. Pat. Nos. 4,839,174 and 4,943,435 disclose that the active agent is incorporated into the monolithic polymer film layer by dissolving the active agent and the polymer into a common solvent, and then solvent-casting the film from the resulting solution. The solvent-casting of monolithic polymer film layers typically requires the evaporation of solvent from the cast film. This has proven to be problematic. Because the film is employed in skin contact end use applications, complete removal of the solvent is necessary. Solvent removal requires the application of elevated temperatures to the polymer film. The removal of solvent by heat-evaporation can strip the lower molecular weight components, including the active agent, from the film, even at temperatures below which these lower molecular weight components volatilize. Reducing the evaporation temperature to levels at which the lower molecular weight components are not stripped, substantially increases the amount of time required for evaporation and results in films having significant levels of residual solvent.

A transdermal patch for the delivery of an active agent having a monolithic polymer film layer into which the active agent is dissolved or suspended without the use of solvents would be highly desirable.

SUMMARY OF THE INVENTION

This need is met by the present invention. It has now be found that active agents can be melt-blended with matrix polymers without first dissolving the polymer and active agent in a common solvent.

Therefore, according to one embodiment of the present invention, a device is provided for the controlled release of an active agent to the skin or mucosa of a host, which device is a laminate of:

(a) a monolithic carrier layer having a first surface and a second surface, the monolithic carrier layer being an active ingredient melt-blended with a thermoplastic matrix polymer capable of controllably releasing the active ingredient, wherein the active ingredient is heat stable at the melt temperature of the matrix polymer and is selected from active agents, active agent enhancers and mixtures thereof;

(b) a backing layer having an inner surface and an outer surface, the inner surface of which is affixed to the laminate so that the active ingredient cannot permeate from the second surface of the carrier layer to the outer surface of the backing layer; and (c) means for affixing the laminate to the skin or mucosa of the host so that the active ingredient is continuously released from the first surface of the carrier layer thereto.

The active ingredient is prevented from permeating the backing layer by either utilizing an active ingredient impermeable backing layer, or by laminating the backing layer to the carrier layer with an active ingredient impermeable adhesive layer, or both.

In preferred aspects of this embodiment, the active ingredient-permeable adhesive layer for affixing the carrier layer to the skin or mucosa of the host includes means for controlling the rate at which the active ingredient is released from the first surface of the carrier layer to the skin or mucosa of the host, which rate-controlling means is affixed to the first surface of the carrier layer. In accordance with one aspect of this embodiment of the invention, the active ingredient permeable adhesive layer is capable of controlling the rate at which the active ingredient is released from the first surface of the carrier layer to the host's skin or mucosa and functions as both the means for affixing the laminate to the host's skin or mucosa and the means for controlling the rate at which the active ingredient is released from the first surface of the carrier layer to the host's skin or mucosa.

The rate-controlling means can alternatively be provided by a rate-controlling polymer layer affixed to the first surface of the carrier layer, which rate-controlling polymer layer is capable of controlling the rate at which the active ingredient is released from the first surface of the carrier layer to the host's skin or mucosa. The rate-controlling polymer layer can be formed from the same polymer as the polymer matrix of the carrier layer, other compatible polymers, and even with incompatible polymers. The rate-controlling polymer layer can be laminated to the carrier layer with an active ingredient permeable adhesive layer. The adhesive layer may or may not control the rate at which the active ingredient is released from the first surface of the carrier layer to the host's skin or mucosa. When the rate-controlling polymer layer is formed from the same polymer or a compatible polymer, the two layers can be laminated by extrusion or coextrusion.

Regardless of how the two layers are laminated, the laminated patch is affixed to the skin or mucosa of the host by an active ingredient permeable adhesive layer adapted to adhere the laminate to the skin or mucosa of the host, affixed to the rate-controlling polymer layer on the surface opposite the carrier layer. Again, this adhesive layer may or may not control the rate at which the active ingredient is released from the first surface of the carrier layer to the host's skin or mucosa.

Preferably, the laminate of the invention will also include a transporting agent or enhancer to promote the penetration of the active agent through the skin. Active agent enhancers suitable for use in transdermal delivery patches are well-known and described in U.S. Pat. No. 4,573,996, the disclosure of which is hereby incorporated herein by reference thereto. The enhancer can be melt-blended with any or all of the thermoplastic matrix polymer, rate-controlling polymer, if present, and active-ingredient permeable adhesives. Enhancers suitable for use with the present invention are heat-stable at the melt temperature of the polymer with which they are combined.

According to another embodiment of the invention, the backing layer of the above-discussed embodiment extends peripherally beyond the carrier layer about the entire periphery thereof so as to create an extended peripheral area of the backing layer, the inner surface of which extended peripheral area of the backing layer is laminated with an adhesive layer to adhere the laminate to the skin or mucosa of the host. In preferred embodiments, the backing layer is affixed to the second surface of the carrier layer by this adhesive layer, so that the adhesive layer is coextensive with the entire inner surface of the backing layer. The adhesive layer may or may not be an active ingredient impermeable adhesive layer, depending upon whether it is desired to prevent the active ingredient from being released radially outwardly through the adhesive layer coating the extended peripheral area of the backing layer.

As with the embodiment discussed above, the laminate can also include means for controlling the rate at which the active ingredient is released from the first surface of the carrier layer. The rate-controlling means can be provided by utilizing an adhesive layer capable of controlling the rate at which the active ingredient is released from the first surface of the carrier layer to the host's skin or mucosa as the active ingredient permeable adhesive layer. Alternatively, the rate-controlling means can be provided by a rate-controlling polymer layer affixed to the first surface of the carrier layer, and then attached to the skin or mucosa of the host on the surface opposite the carrier layer by an active ingredient permeable adhesive layer that may or may not control the rate at which the active ingredient is released from the first surface of the carrier layer to the host's skin or mucosa. An active agent enhancer to promote the penetration of the active agent through the skin can likewise be melt-blended in the rate-controlling polymer layer or either active ingredient permeable adhesive layers.

In another embodiment of the present invention, the active ingredient in the monolithic carrier layer is an active agent enhancer and the laminate further includes a rate-controlling polymer layer having an inner surface and an outer surface, the rate-controlling polymer layer being an active agent melt-blended with a thermoplastic rate-controlling polymer capable of controllably releasing the active agent, wherein the active agent is heat-stable at the melt-temperature of the rate-controlling polymer, and wherein the inner surface of the rate-controlling polymer layer is affixed to the first surface of the carrier layer; and an active ingredient permeable adhesive layer affixed to the outer surface of the rate-controlling polymer layer for attaching the laminate to the skin or mucosa of the host, so that the active agent enhancer is continuously released from the first surface of the carrier layer through the rate-controlling polymer layer and then released with the active agent from the outer surface of the rate-controlling polymer layer through the active agent permeable adhesive layer to the skin or mucosa of the host.

In yet another embodiment of the present invention, a plurality of the above-described laminates are combined on a single device whereby a multiple-compartment assembly for applying a plurality of active agents to the skin or mucosa of a host is provided. Assemblies in accordance with this embodiment of the present invention combine a removable liner layer including a first surface and a second surface with a bottom layer including a first surface and a second surface and more than one of the laminates of the invention therebetween. The first surface of the liner layer is a releasable surface, which is heat sealed at least at a location between the laminates so as to physically separate the laminates prior to removal of the removable liner layer from the bottom layer, whereby removal of the removable liner layer eliminates the heat seal.

The laminates include all aspects of both embodiments of the above-described laminate of a monolithic carrier layer, a backing layer, and means for affixing the laminate to the skin or mucosa of the host. The backing layer of each laminate is affixed to the first surface of the bottom layer, and the means for securing each laminate to the skin or mucosa of the host is affixed to the first surface of the liner layer.

In still yet another embodiment of the present invention, a method is provided for assembling a device for the controlled release of an active agent to the skin or mucosa of a host, which method includes the steps of:

(a) melt-blending a thermoplastic matrix polymer capable of controllably releasing an active ingredient with an active ingredient that is heat stable at the melt temperature of the matrix polymer, so that a melt-blend of the active ingredient and thermoplastic matrix polymer is formed, wherein the active ingredient is selected from active agents, active agent enhancers and mixtures thereof;

(b) forming the melt-blend into a monolithic carrier layer having a first surface and a second surface;

(c) providing a backing layer having an inner surface and an outer surface and laminating the second surface of the carrier layer to the inner surface of the backing layer so that a laminate of the carrier layer and backing layer is formed wherein the active ingredient cannot permeate from the second surface of the carrier layer to the outer surface of the backing layer; and (d) providing the laminate with an active ingredient permeable adhesive layer for securing the laminate to the skin or mucosa of the host so that the active ingredient is controllably released from the first surface of the carrier layer thereto.

In accordance with one aspect of this embodiment of the invention, the step of providing the laminate with means for securing the laminate to the skin or mucosa of the host includes the step of laminating an active ingredient permeable adhesive layer to the first surface of the carrier layer. According to another aspect of this embodiment of the invention, the method further includes the step of affixing to the first surface of the carrier layer, means for controlling the rate at which the active ingredient is released from the first surface of the carrier layer to the skin or mucosa of the host. The rate-controlling means may be provided by utilizing an active ingredient permeable adhesive layer capable of controlling the rate at which the active ingredient is released from the first surface of the carrier layer to the host's skin or mucosa.

Alternatively, the rate-controlling means can be provided by laminating to the first surface of the carrier layer, a rate-controlling polymer layer capable of controlling the rate at which the active ingredient is released from the first surface of the carrier layer to the host's skin or mucosa. The laminating step may include the step of laminating the rate-controlling polymer layer to the carrier layer with an active ingredient permeable adhesive, or, if the two polymer layers are compatible, the laminating step includes the step of extruding, and preferably coextruding, the rate-controlling polymer layer together with the carrier layer. Either laminating step further includes the step of applying to the rate-controlling polymer layer on the surface opposite the carrier layer, an active ingredient permeable adhesive layer adapted to adhere the laminate to the skin or mucosa of the host. The active ingredient permeable adhesive may or may not control the rate at which the active ingredient is released from the first surface of the carrier layer to the host's skin or mucosa.

According to another aspect of this embodiment of the invention, the step of laminating the second surface of the carrier layer to the inner surface of the backing layer includes the step of laminating the second surface of the carrier layer to the inner surface of a backing layer having a greater surface area than the carrier layer so that the greater surface area of the backing layer extends peripherally beyond the carrier layer about the entire periphery thereof so as to create an extended peripheral area of the backing layer. The step of providing the laminate with means for securing the carrier layer to the skin or mucosa of the host then includes the step of laminating the extended peripheral area of the inner surface of the backing layer with an adhesive layer to adhere the laminate thereto.

Alternatively, the step of laminating the extended peripheral inner surface area of the backing layer may include the step of coating the entire inner surface of the backing layer with an adhesive layer prior to laminating the inner surface to the second surface of the carrier layer, so that when the second surface of the carrier layer is laminated to the inner surface of the backing layer, the layers are secured by the adhesive layer, which also extends peripherally beyond the carrier layer about the entire periphery thereof coextensively with the extended peripheral area of the backing layer. The adhesive layer thus both secures the laminate to the skin or mucosa of the host and laminates the second surface of the carrier layer to the inner surface of the backing layer. The adhesive layer may or may not be an active ingredient impermeable adhesive layer, depending upon whether or not it is desirable for the active ingredient to permeate radially outwardly through the extended peripheral adhesive layer.

According to another aspect of this embodiment of the invention, an active agent enhancer is incorporated into one or more of the rate-controlling polymer or the active agent permeable adhesives, preferably by melt-blending. According to still yet another aspect of this embodiment, the active ingredient of the thermoplastic matrix polymer includes an active agent enhancer, and the method further includes the steps of:

(a) melt-blending a thermoplastic rate-controlling polymer capable of controllably releasing an active agent that is heat stable at the melt temperature of the rate-controlling polymer so that a melt-blend of the active agent and the thermoplastic rate-controlling polymer is formed;

(b) forming the melt-blend containing the active agent into a monolithic rate-controlling polymer layer having an inner surface and an outer surface; and (c) laminating the inner surface of the rate-controlling polymer layer to the first surface of the carrier layer; wherein, the step of providing the laminate with an active ingredient permeable adhesive layer for securing the laminate to the skin or mucosa of the host includes coating the outer surface of the rate-controlling polymer layer with an active ingredient permeable adhesive layer for securing the laminate to the skin or mucosa of the host, so that the active agent enhancer is continuously released from the first surface of the carrier layer through the rate-controlling polymer layer and then released with the active agent from the outer surface of the rate-controlling polymer layer through the adhesive layer to the skin or mucosa of the host.

According to yet another aspect of this embodiment of the invention, a method is provided for combining a plurality of the above-described laminates on a single device to provide a multiple-compartment assembly for applying a plurality of active agents to the skin or mucosa of a host. Methods in accordance with this aspect of this embodiment of the invention further include the steps of:

(a) providing a removable liner layer having a first surface and a second surface, wherein the first surface of the liner layer is a releasable surface;

(b) providing a bottom layer having a first surface and a second surface;

(c) disposing more than one laminate for the controlled release of an active agent to the skin or mucosa of a host between the first surface of the bottom layer, and the first surface of the liner layer, wherein the backing layer of each laminate is affixed to the first surface of the bottom layer and the means for securing each laminate to the skin or mucosa of the host is affixed to the liner layer; and (d) releasably heat sealing the first surface of the liner layer to the first surface of the bottom layer at least at a location between two of the laminates so as to physically separate at least two laminates prior to removal of the removable liner layer from the bottom layer, whereby removal of the liner layer eliminates the heat seal.

The present invention includes the discovery that thermoplastic polymers suitable for use as carrier layers and rate-controlling layers can be melt-blended with active agents and active agent enhancers that are heat stable at the melt temperature of the polymer. The polymer blends can be formed into carrier layers and rate-controlling polymer layers that can be incorporated into a transdermal delivery patch from which the active agent is controllably released. The polymer layers thus provided are obtained without first dissolving or suspending the active agent or active agent enhancer with the polymer into a common solvent, thereby eliminating the undesirable properties resulting therefrom. Transdermal delivery patches incorporating the polymer laminates of the present invention can also be prepared more economically because less loading of the active agent is required to obtain a desired dosage rate.

BRIEF DESCRIPTION OF THE DRAWINGS

A more complete appreciation of the invention and many other intended advantages can be readily attained by reference to the following detailed description when considered in connection with the following drawings, wherein.

It should be noted that the drawings are not necessarily to scale, but that certain elements have been expanded to show more clearly the various aspects of the present invention and their advantages.

DETAILED DESCRIPTION OF THE PREFERRED EMBODIMENTS

Figure 1:
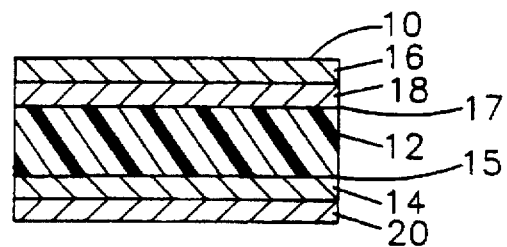
FIG. 1 shows a side, cross-sectional view of a device according to the present invention.

Referring to the figures, in which like numerals refer to like portions thereof, FIG. 1 shows a device of the present invention. FIG. 1 shows a cross-section of the entire transdermal delivery patch device 10 of the present invention in its sealed configuration. The active ingredient, which may include an active agent, an active agent enhancer, or both, is contained in a monolithic thermoplastic polymer matrix carrier layer 12. The active agent enhancer functions to promote the penetration of the active agent through the skin. An active agent permeable skin contact adhesive layer 14 is applied to surface 15 of the carrier layer 12, providing a means for affixing the device to the skin or mucosa of the host. Backing layer 16 is affixed by adhesive layer 18 to the surface 17 of the carrier layer 12 opposite the active agent permeable adhesive layer 14. Either the backing layer 16, or the adhesive layer 18, or both, should be impermeable to the active ingredient so that the active ingredient does not permeate outwardly through the backing surface 10 of the backing layer.

Instead, the active ingredient is continuously released from the surface 15 of the carrier layer 12 through the active ingredient permeable skin contact adhesive layer 14 to the skin or mucosa of the host. Protective liner 20 covers the active ingredient permeable skin contact adhesive layer 14 prior to use to prevent the release of the active ingredient and to protect the skin contact adhesive layer, a pressure-sensitive adhesive, from inactivation by ambient dust or other contaminants.

Figures 2, 2A:
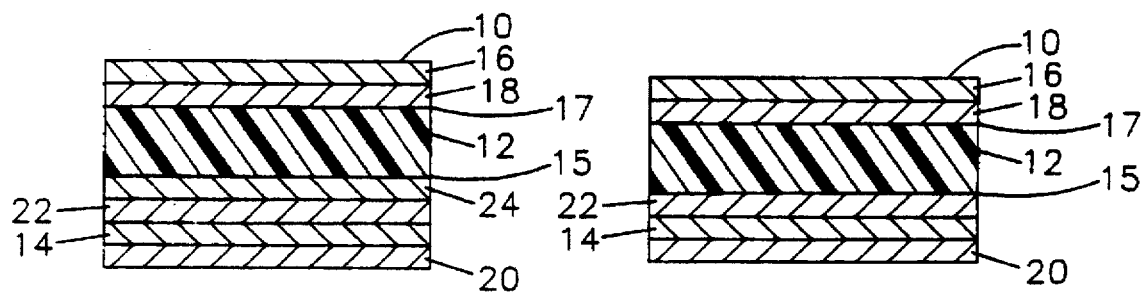
FIG. 2–2a show side, cross-sectional views of two other related embodiments of the present invention.

The embodiment shown in FIG. 2 differs from that in FIG. 1 only in that a rate-controlling polymer layer 22 is affixed to surface 15 of carrier layer 12 by active ingredient permeable adhesive layer 24 to provide a means for controlling the rate at which the active ingredient is released from the surface 15 of carrier layer 12 to the skin or mucosa of the host. In FIGS. 1 and 2, any or all of the adhesive layers 14 or 24, or the rate-controlling polymer layer 22 may optionally include an active agent enhancer to promote the penetration of the active agent through the skin.

Active ingredient permeable skin contact adhesive layer 14 is applied to the surface of the rate-controlling polymer layer 22 opposite the carrier layer 12 to provide a means for affixing the device to the skin or mucosa of the host. Means for controlling the rate at which the active ingredient is released from the surface 15 of the carrier layer 12 to the skin or mucosa of the host can also be provided to the embodiment of FIG. 1 by utilizing an adhesive capable of controlling the rate at which the active ingredient is released from the surface 15 of the carrier layer 12 to the host's skin or mucosa as the active ingredient permeable skin contact adhesive layer 14.

The embodiment shown in FIG. 2a differs from that in FIG. 2 in that rate-controlling polymer layer 22 is affixed to surface 15 of carrier layer 12 by extrusion, or preferably, coextrusion, of the two layers together. Means for affixing the device to the skin or mucosa of the host is provided by active ingredient permeable skin contact adhesive layer 14 applied to the surface of the rate-controlling polymer layer 22 opposite the carrier layer 12.

Figure 3:
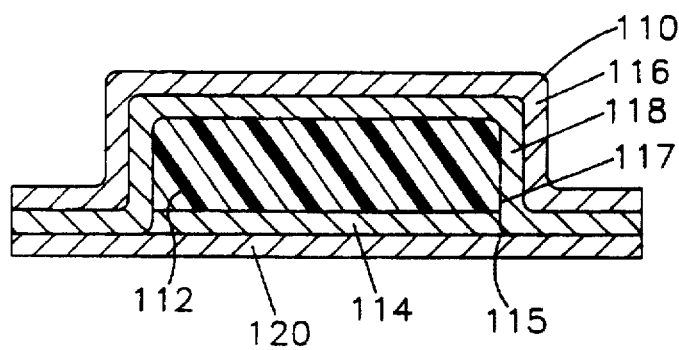
FIG. 3 shows a side, cross-sectional view of another embodiment of the present invention.
Figure 4:
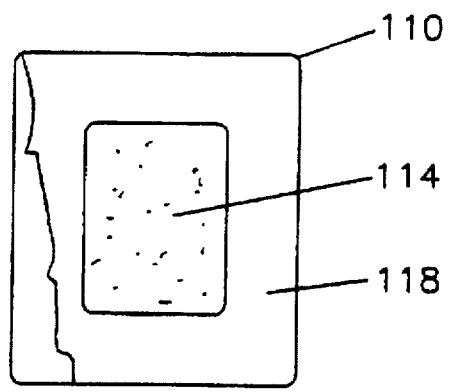
FIG. 4 shows a top, elevational, partially torn away view of another embodiment of the present invention showing the liner layer thereof.

The device 110 shown in FIGS. 3 and 4 is somewhat similar to that shown in FIG. 1. Monolithic polymer matrix carrier layer 112 containing the active ingredient has a backing layer 116 affixed to surface 117 by adhesive layer 118. Again, either or both the backing layer 116 or the adhesive layer 118 should be impermeable to the active agent. The backing layer 116 and the adhesive layer 118 have a sufficient surface area and are the shape so that, when they are attached to the carrier layer 112, they overlap the carrier layer 112 completely. Thus, the adhesive surface adheres to the carrier layer 112 so that the adhesive layer 118 surrounds the perimeter of the carrier layer 112 and the active ingredient permeable skin contact adhesive layer 114 applied to surface 115 thereof.

The active ingredient permeable adhesive layer 114 and the adhesive layer 118 are positioned so that when the protective liner 120 is removed, the two adhesive layers can be applied to the skin or mucosa and thus function as a means for affixing the device to the skin or mucosa of the host. The active ingredient is thus released from surface 115 of carrier layer 112 through the active ingredient permeable skin contact adhesive layer 114 to provide a continuous dose of the active ingredient therethrough, but cannot permeate through the backing layer 116 or when the adhesive layer 118 is active ingredient impermeable, radially outwardly therethrough.

Figure 5:
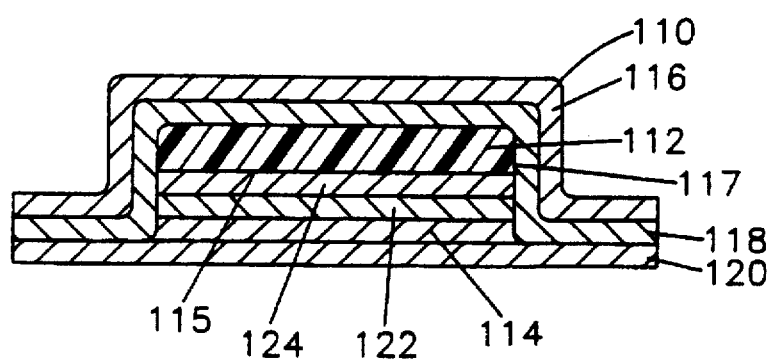
FIG. 5 shows a side, cross-sectional view of the embodiment of the invention shown in FIG. 4.

The embodiment shown in FIG. 5 differs from that shown in FIGS. 3 and 4 only in that a rate-controlling polymer layer 122 is affixed to surface 115 of carrier layer 112 by active ingredient permeable adhesive layer 124, thus providing a means for controlling the rate at which the active ingredient is released from the surface 115 of the carrier layer 112 to the skin or mucosa of the host. The surface area of the rate-controlling polymer layer 122 and the active ingredient permeable adhesive layer 124 is such that the backing layer 116 and adhesive layer 118 also overlap and surround the perimeters of the rate-controlling polymer layer 122 and the active ingredient permeable adhesive layer 124.

Means for controlling the rate at which the active ingredient is released from the surface 115 of the carrier layer 112 to the skin or the mucosa of the host can also be provided to the embodiment of FIGS. 3 and 4 by utilizing an adhesive capable of controlling the rate at which the active ingredient is released from the surface 115 of the carrier layer 112 to the host's skin or mucosa as the active ingredient permeable skin contact adhesive layer 114. The devices shown in FIGS. 3–5 may optionally include an enhancer to promote the penetration of the active ingredient through the skin. The enhancer may be included with any or all of the carrier layer 112, the rate-controlling polymer layer 122, or the adhesive layers 114 or 124, whichever are present.

Figure 6:
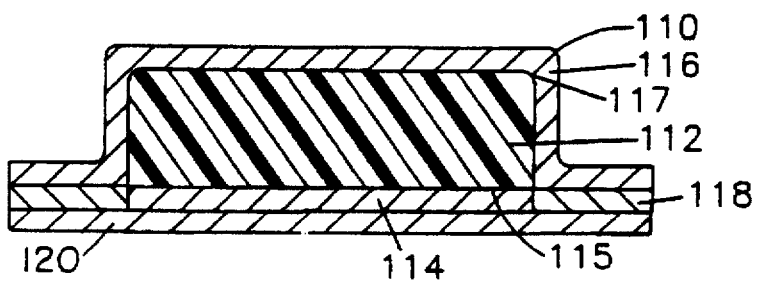
FIGS. 6–6a show side, cross-sectional views of two other related embodiments of the present invention.

The embodiment shown in FIG. 6 differs from that shown in FIG. 3 and 4 only in that backing layer 116 is affixed to surface 117 of monolithic polymer matrix carrier layer 112 by extrusion and preferably coextrusion of the two layers together. Therefore, backing layer 116 is impermeable to the active ingredient so that the active ingredient does not permeate outwardly therethrough. Means for affixing the device to the skin or mucosa of the host is provided by adhesive layer 118, which surrounds the perimeter of the carrier layer 112 and by active ingredient permeable skin contact adhesive layer 114, applied to surface 115 of carrier layer 112 and positioned with respect to adhesive layer 118 so that when the protective liner 120 is removed, the two adhesive layers can be applied to the skin or mucosa.

Figure 6A:
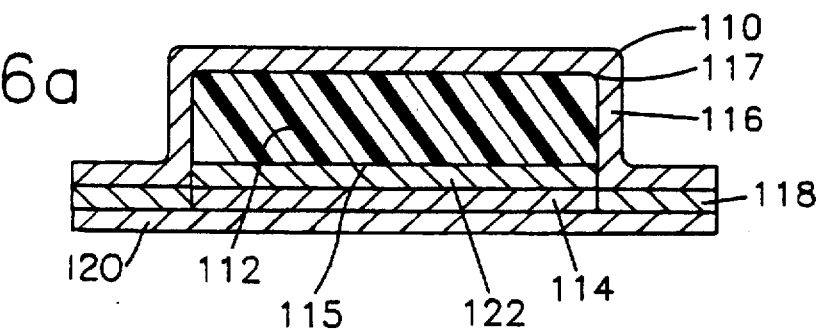

The embodiment shown in FIG. 6a differs from that shown in FIG. 6 in that rate-controlling polymer layer 122 is affixed to surface 115 of carrier layer 112 by extrusion, and preferably coextrusion, of the two layers together. Means for affixing the device to the skin or mucosa of the host is provided by adhesive layer 118, which surrounds the perimeter of carrier layer 112 as in FIG. 6, as well as polymer layer 122, and by active ingredient permeable skin contact adhesive layer 114 which is applied to surface 115 of carrier layer 112 in addition to adhesive layer 118.

The devices shown in FIGS. 6 and 6a may also optionally include an active agent enhancer with any or all of the rate-controlling polymer layer 122 or the adhesive layer 114, whichever are present.

Figure 7:
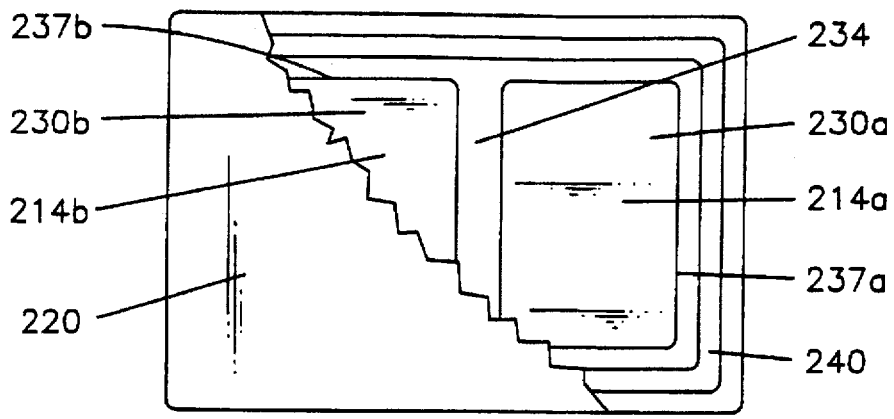
FIG. 7 shows a top, elevational, partially torn away view of another embodiment of the present invention showing the liner layer thereof.
Figure 8:
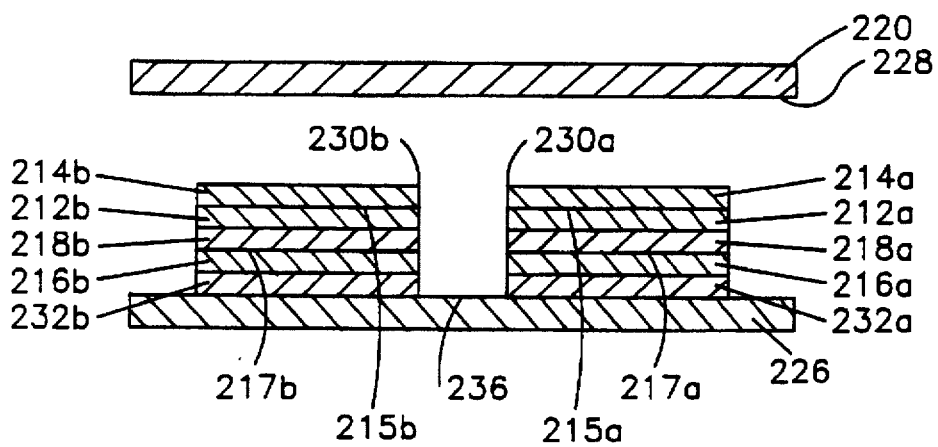
FIG. 8 shows a side, cross-sectional view of the embodiment of the invention shown in FIG. 7.

The device 210 shown in FIGS. 7 and 8 represents the substitution of the embodiment of FIG. 1, with the protective liner removed, namely the combination of the backing layer, carrier layer, and adhesive layer, for the active agent carrying members of the device disclosed in commonly owned U.S. Pat. No. 5,064,422, the disclosure of which is hereby incorporated herein by reference thereto. The embodiment depicted in FIGS. 7 and 8 provides a multiple-compartment assembly for applying a plurality of active agents or enhancers therefor to the skin or mucosa of a host, in which each compartment contains a monolithic thermoplastic matrix polymer carrier layer capable of controllably releasing the active agent or active agent enhancer. FIG. 7 shows a top, elevational partially torn-away view of the device in which the liner layer is partially exposed, and FIG. 8 shows a cross-section of the entire device in its sealed configuration.

Referring first to FIG. 8, protective liner layer 220 functions, as in the prior embodiments, to protect the active agents as well as any polymer or adhesive layers used in the device of this invention prior to use, and to render them transportable while not interfering with their ultimate application. Furthermore, in accordance with this invention, the liner layer 220 must be heat sealed to the bottom layer 226 in order to not only protect the active agents, and enhancers, if present, but to maintain them separate from each other in order to compartmentalize the device.

Liner layer 220 must have an inner surface 228 that is releasable with respect to the materials or layers with which it is initially in contact, namely the active agent permeable skin contact adhesive layers 214a and 214b on the active agent carrying members 230a and 230b. The liner layer 220 therefore should include a release coating, which release coating is essentially conventional.

The active agent carrying members 230a and 230b are secured on the bottom layer 226 by adhesive layers 232a and 232b. The bottom layer 226 should be flexible enough to generally follow the contour of the area of the host where the device is to be applied. On the other hand, it should have enough strength and substance so as to serve its function of carrying the active agent carrying members 230a and 230b without wrinkling. With respect to the active agent carrying members 230a and 230b, in the embodiment shown in FIG. 8, they basically comprise monolithic carrier layers 212a and 212b of the same or different active ingredients melt-blended with thermoplastic matrix polymers capable of controllably releasing the active ingredients. One of monolithic carrier layers 212a and 212b can contain an active agent enhancer for the active agent contained in the other of the carrier layers.

As with the embodiment of FIGS. 1 and 2, active ingredient permeable skin contact adhesive layers 214a and 214b are applied to surfaces 215a and 15b of carrier layers 212a and 212b, providing a means for applying the carrier layers to the skin or mucosa of the host. Backing layers 216a and 216b are affixed by adhesive layers 218a and 218b to surfaces 217a and 217b of carrier layers 212a and 212b opposite the active ingredient permeable skin contact adhesive layers 214a and 214b. Again, either the backing layers 216a and 16b, or the adhesive layers 218a and 218b, should be impermeable to the active ingredient. The active agent enhancer may be blended with either or both of the adhesive layers 214a and 214b. Protective liner 220 covers active ingredient permeable skin contact adhesive layers 214a and 214b.

The active agent carrying members 230a and 230b must be maintained in contact with bottom layer 226 by adhesive layers 232a and 232b with sufficient strength to maintain same when the active agent carrying members 230a and 230b are exposed or uncovered by removing liner layer 220 therefrom. At the same time, this bond must be sufficiently weak in relative terms so that bottom layer 226 will readily peel off or be removable from the active agent carrying members 230a and 230b after the active agent carrying members have been applied to the skin by means of adhesive layers 214a and 214b. This is accomplished by the relationship between the strength of adhesive layers 232a and 232b on the one hand, and 214a and 214b on the other hand. In this regard, the adhesive layers 232a and 232b have a coefficient of adhesion which is less than the coefficient of adhesion of the adhesive layers 214a and 214b. In this manner, upon application of the active agent carrying members 230a and 230b to the patient with the adhesive layers 214a and 214b, the active agent carrying members will adhere to the patient and be simultaneously removed from the carrier layer by way of adhesive layers 232a and 232b.

In order to produce the overall device shown in FIG. 7, the liner layer 220 is brought into face-to-face contact with the bottom layer 226 with the active agent carrying members 230a and 230b therebetween. Although the liner layer 220 is secured by adhesive layers 214a and 214b covering the faces of active agent carrying members 230a and 230b which cover a substantial portion of the area represented by bottom layer 226, heat seals are also provided between the liner layer 220 and the bottom layer 226, at a location between the active agent carrying members 230a and 230b. The location of the heat seal is shown by reference numeral 234 in FIG. 7. The heat seal is provided as a "peelable seal" between the liner layer 220 and the bottom layer 226.

While the precise compositions of the carrier and liner layers are discussed in more detail in this application, the nature of the facing surfaces 228 and 236 (shown in FIG. 8) of these two layers will be significant in creating such a "peelable seal." In this regard, it should be noted, for example, when the two facing layer comprise inner polyethylene layers, the creation of such a "peelable seal" is then accomplished in the manner described in U.S. Pat. No. 4,710,191, the disclosure of which is incorporated herein by reference thereto.

In particular, in that patent it is disclosed that such a "peelable seal" can be created by the incorporation of a release coating on the inner surface of a layer such as liner layer 220 so as to render the heat-sealed area then created between these two layers, in this case between liner layer 220 and bottom layer 226, by weakening the thermal bond created therein. It is also disclosed in this patent that one alternative for achieving this result is to employ two different materials as the inner layers for the liner layer 220 and the bottom layer 226, such as polyethylene and polypropylene, etc. In such a case, the release coating would then be required on the inner surface of the liner layer 220, at least for the purposes of creating such a "peelable seal" at these locations.

In general, the purpose of the "peelable seal" is not only to separate the device into individual compartments 237a and 237b bearing the active agent carrying members 230a and 230b; at the same time, these "peelable seals" permit the ready separation of the liner layer 220 and the carrier layer 226. For example, if two polyethylene layers were heat sealed together in the manner described above without a release coating, such as a silicon layer therebetween, the two layers would essentially melt together, and such separation would not be readily achieved. Thus, the nature of these "peelable seals" is an important feature of the present invention.

Referring again to FIG. 7, "peelable seals" which critically separate the two active agent carrying members 230a and 230b are located not only therebetween, but extend along path 238 so as to surround both active agent carrying member 230a and active agent carrying member 230b. Furthermore, a separate continuous heat seal 240 separate from heat seal 238 surrounds the entire device including both active agent carrying members 230a and 230b.

In this manner, each of the active agent carrying members is isolated prior to separation of the liner layer 220 from the bottom layer 226. The significance of this separation is that when different active agents are to be applied in connection with active agent carrying members 230a and 230b, it will generally be necessary to carefully specify each of the formulations for each of the active agents. Delivery rate is a critical element in the use of any such active agents, and any premature migration or mixing of the active agents will alter the delivery rate with obvious untoward consequences. Placement of the heat seals described above between the active agent carrying members 230a and 230b, however, will prevent such migration or mixing, and thus permit maintenance of the critical and carefully devised delivery rates and potency for each of the separate active agents therein, and at the same time will have no adverse effect upon use of this device, i.e., the carrier and liner layers are still readily separated when it is desired to apply these active agents to the patient's skin.

It is further noted that the placement of such heat seal between the active agents hereof provides an area therebetween which could be used for separation of the device into separate devices. This can be facilitated by merely widening the area of this peelable heat seal between the active agent carrying members, for example, to provide a ¼ inch heat-seal strip therebetween. Thus, by using scissors to cut through such enlarged areas 238 prior to separation of the carrier layer from the liner layer, two separate devices can be readily provide from a single device manufactured therein.

Figure 9:
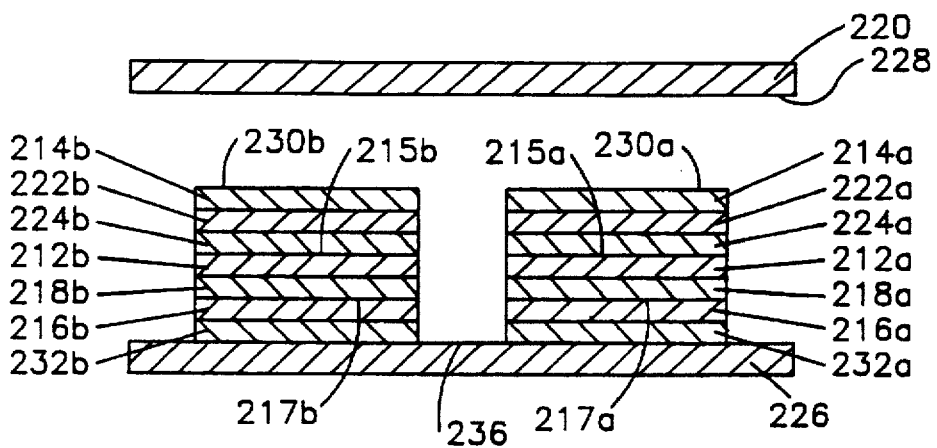
FIG. 9 shows a side, cross-sectional view of another embodiment of the present invention.

The embodiment shown in FIG. 9 differs from that shown in FIGS. 7 and 8 only in that rate-controlling polymer layers 222a and 222b are affixed to surfaces 215a and 215b of carrier layers 212a and 212b by active ingredient permeable adhesive layers 224a and 224b to provide a means for controlling the rate at which the active ingredients are released from the surfaces 215a and 215b of the carrier layers 212a and 212b to the skin or mucosa of the host. Active ingredient permeable skin contact adhesive layers 214a and 214b are applied to the surface of the rate-controlling polymer layers 222a and 222b opposite the carrier layers 212a and 212b to provide a means for affixing the devices to the skin or mucosa of the host. Active agent enhancers can also be blended with the polymer of the rate-controlling polymer layers 222a and 222b, and with the active ingredient permeable adhesive layers. If the rate-controlling polymer and the carrier polymer are compatible, the two layers can be extruded, and preferably, coextruded, together.

Means for controlling the rate at which the active agents are released from the surfaces 215a and 215b of carrier layers 212a and 212b to the skin or mucosa of the host can also be provided to the embodiments of FIGS. 7 and 8 by utilizing an adhesive capable of controlling the rate at which the active agents are released from the surfaces 215a and 215b of the carrier layers 212a and 212b to the skin or mucosa as the active agent permeable skin contact adhesive layers 214a and 214b. One or all of the active agent carrier members can include a polymer or adhesive rate-controlling means.

Figure 10:
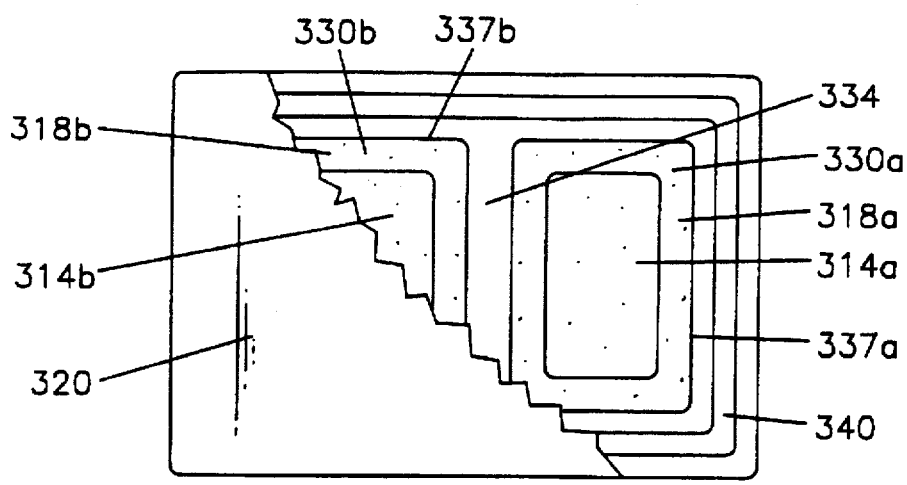
FIG. 10 shows a top, elevational, partially torn away view of another embodiment of the present invention showing the liner layer thereof.
Figure 11:
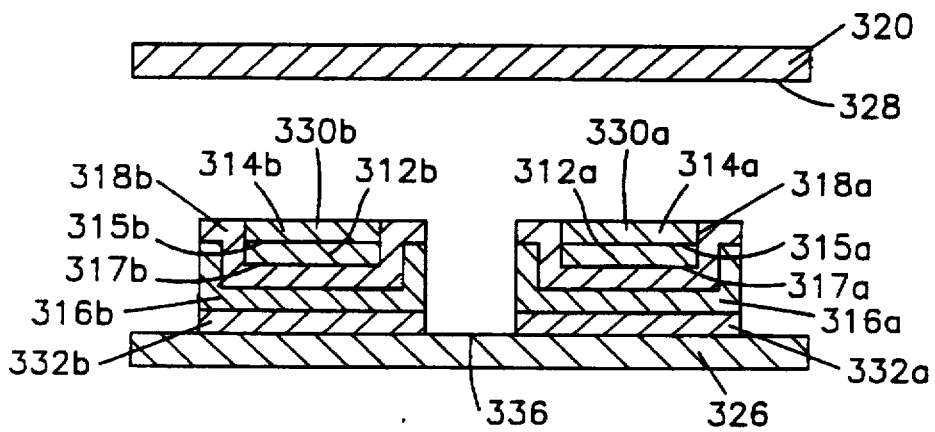
FIG. 11 shows a side, cross-sectional view of the embodiment of the invention shown in FIG. 10.

The embodiment shown in FIGS. 10 and 11 combine the elements of the embodiments depicted in FIGS. 3, 4, 7 and 8. Carrier layers 312a and 312b containing the same or different active ingredients have backing layers 316a and 316b affixed to surfaces 317a and 317b by adhesive layers 318a and 318b. Again, either the backing layers 316a and 316b or the adhesive layers 318a and 318b, or both, should be impermeable to the active ingredient. The backing layers 316a and 316b and the adhesive layers 318a and 318b have sufficient surface areas and are of a shape so that, when they are attached to the carrier layers 312a and 312b, they overlap the carrier layers 312a and 312b completely. Thus, the adhesive surfaces adhere to the carrier layers so that the adhesive layers 318a and 318b surround the perimeters of the carrier layers 312a and 312b and the active ingredient permeable skin contact adhesive layers 314a and 314b applied to surfaces 315a and 315b thereof.

The active ingredient permeable skin contact adhesive layers 314a and 314b and the adhesive layers 318a and 318b are positioned so that when the protective liner 320 is removed, the adhesive layers can be applied to the skin or mucosa, and thus function as a means for affixing the device to the skin or mucosa of the host. The active ingredients are thus released from the surfaces 315a and 315b of carrier layers 312a and 312b through the active ingredient permeable skin contact adhesive layers 314a and 314b to provide a continuous dose of the active ingredients therethrough, but cannot permeate through the active ingredient impermeable backing layers 316a and 316b, or, when the adhesive layers 318a and 318b are impermeable to the active ingredient, radially outwardly therethrough. As with the other depicted embodiments, active ingredient enhancers can be blended with any or all of the adhesive layers 314a and 314b.

Figure 12:
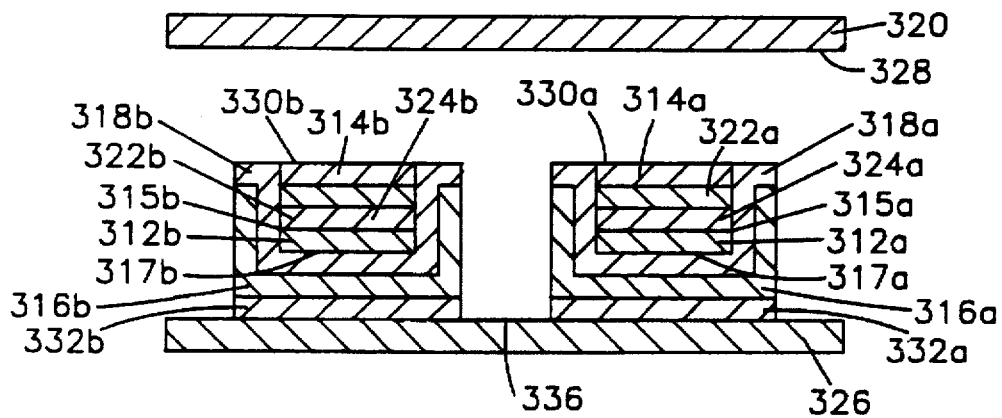
FIG. 12 shows a side, cross-sectional view of another embodiment of the present invention.

The embodiment shown in FIG. 12 differs from that shown in FIGS. 10 and 11 only in that rate-controlling polymer layers 322a and 322b are affixed to surfaces 315a and 315b of carrier layers 312a and 321b by active ingredient permeable adhesive layers 324a and 324b as described above with respect to the embodiment of FIG. 5. Active ingredient permeable skin contact adhesive layers 314a and 314b of FIGS. 10 and 11 can also be utilized as means for controlling the rate at which the active ingredient is released from the surfaces 315a and 315b of the carrier layers 312a and 312b to the skin or mucosa of the host for the embodiment of FIGS. 10 and 11 as described above with respect to the embodiment of FIGS. 3 and 4. Likewise, the embodiments of FIGS. 6 and 6a can be adapted to the embodiment of FIGS. 10 and 11. As with the embodiments of FIGS. 5, 6a and 9, an active agent enhancer can be blended with the polymer of the rate-controlling polymer layer.

The embodiments depicted in FIGS. 2, 5, 6a, 9 and 12 can also be formulated and assembled so that the active agent is included in the rate-controlling polymer layer when an active agent enhancer is included in the carrier layer. Thus, referring to FIG. 2, the active agent can be contained in rate-controlling polymer layer 22, with an active agent enhancer contained in the monolithic thermoplastic polymer matrix carrier layer 12. Likewise, in the embodiments depicted in FIGS. 5 and 6a, the active agent can be contained in polymer layer 122 with an active agent enhancer contained in carrier layer 112. The active agent can also be included with the polymer layers 222a and 222b and 322a and 322b of FIGS. 9 and 12, with an active agent enhancer contained in carrier layers 212a and 212b or 312a and 312b.

The active agent can also be included in both the carrier layer and rate-controlling polymer layer. Such embodiments of the invention can include laminates that do not utilize an active agent enhancer, as well as laminates that have an active agent enhancer in one or more of the carrier layer, rate-controlling polymer layer, and active agent permeable adhesive layers.

The present invention also includes embodiments in which active agent or the active agent enhancer are included in layers in which they have not been melt-blended, which layers may also be non-polymeric. Such layers are instead prepared and assembled into the laminate by conventional methods using prior art materials that are well-known to those of ordinary skill in the art. Laminates in accordance with the present invention, however, will at the least include a carrier layer of a thermoplastic matrix polymer melt-blended with an active agent, an active agent enhancer, or both.

In addition, the present invention further includes embodiments in which more than one carrier layer is present or more than one rate-controlling polymer layer is present, or both, in any order, provided that at least one rate-controlling polymer layer, if present, is situated between a carrier layer and the skin or mucosa of the host. At least one carrier layer is melt-blended with an active agent, active agent enhancer, or both, otherwise the other layers may include an active agent, active agent enhancer, or both, or may be substantially free of an active agent or active agent enhancer. The active agent or active agent enhancer may be melt-blended with the other layers or combined with the other layers by conventional methods.

When an active agent or active agent enhancer is present in more than one layer, the active agent or active agent enhancer of each layer may be the same or different. The present invention also includes embodiments in which more than one active agent or active agent enhancer is included in a carrier layer or rate-controlling polymer layer.

The backing layer is preferably a thin film or sheet. In many instances, because of the area of skin to which the device is to be attached, the device, and therefore the backing layer, is flesh colored for cosmetic reasons. Preferably, it is a clear polyester layer, which is occlusive with respect to the active agent or drug, but it can be dyed various colors, or include printed matter thereon. The backing layer normally provides support and a protective covering for the device.

The backing layer is preferably made of a material or combination of materials that is substantially impermeable to the layer or layers with which it can be in contact, i.e., to the carrier layer and the active ingredient contained therein, the adhesives, etc. However, a primary objective is to prevent seepage of the active ingredient through the backing layer of the device so, if the backing layer is coated on the surface in contact with the remainder of the device with an adhesive layer that is active ingredient impermeable, this impermeable adhesive layer will perform this purpose even if the backing layer is not totally impermeable to the active ingredient. Thus, it is not necessary in all instances that the backing layer be impermeable to the active ingredient, although in most instances it normally is, and when it is not a layer providing this barrier function, such as an active ingredient impermeable adhesive layer, will be situated between the backing layer and the carrier layer. By substantially impermeable, it is meant that the other components in contact with the backing layer or component under consideration will not appreciably permeate through such layer or component for the normal period of use and storage of the device.

The actual material used for the outer surface layer, i.e., referring to FIG. 1, for example, the backing layer 16, will depend on the properties of the materials in contact therewith. Some suitable materials include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride (e.g., SARAN), paper, cloth and aluminum foil. The material used is preferably impermeable to the active ingredient. The material which forms this backing layer may be flexible or non-flexible. Preferably, a flexible backing layer is employed to conform to the shape of the body member to which the device is attached.

Preferably, the material which forms the backing layer, such as layer 16 of FIG. 1, is a film or a composite film. The composite can be a metallized (e.g., aluminized) film or a laminate of two or more films or a combination thereof. For example, a laminate of polyethylene terephthalate and polyethylene or a polyethylene/metallized polyethylene terephthalate/polyethylene laminate can be employed. The preferred polymers include polyethylene, polypropylene, polyvinyl chloride, polyethylene terephthalate and polyvinylidene chloride (SARAN). Most particularly, a highly preferred composition of the present invention employs highly occlusive layers of polyethylene terephthalate or polyvinylidene chloride (SARAN) as a backing layer such as backing member 16 of FIG. I in conjunction with a carrier layer such as carrier layer 12 of FIG. 1 of the PEBAX materials discussed below. Thus, while the polyethylene terephthalate or SARAN component is highly occlusive with respect to the materials in questions, it also is relatively stiff or hard, and therefore use of a very soft and flexible film, such as the PEBAX discussed below for a carrier layer such as carrier layer 12 of FIG. 1, provides an excellent combination from the point of view of comfort and application to the user.

As described above, the backing layer is affixed to the carrier layer by an adhesive layer. For example, with respect to FIG. 1, backing layer 16 is affixed to surface 17 of carrier layer 12 by adhesive layer 18. With respect to FIG. 3, backing layer 116 is affixed to surface 117 of carrier layer 112 by adhesive layer 118. In both embodiments, as discussed above, the adhesive layer may be active ingredient impermeable to prevent seepage of the active ingredient from the carrier layer to the backing layer, and should be active ingredient impermeable when the backing layer is not. In the embodiment of FIG. 3, the adhesive layer 118 and the backing layer 116 extend peripherally beyond the carrier layer 112 about the entire periphery thereof so as to create an extended peripheral area of the backing layer 116 with the adhesive layer 118 peripherally extending beyond the carrier layer 112 coextensively with the extended peripheral area of the backing layer 116. Therefore, another purpose of the adhesive layer 118 in the embodiment of FIG. 3 is to secure the device to the skin or mucosa.

Thus, any adhesive capable of providing adhesion of the backing layer to the carrier layer will be suitable for use with the embodiment of FIG. 1 of the present invention, and any such adhesive that is also capable of providing adhesion to the skin or mucosa will also be suitable for use with the embodiment of FIG. 3 of the present invention. The degree of impermeability of the adhesive layer to the active ingredient would depend upon the active ingredient and the backing layer. Preferably, the adhesive layer is a pressure-sensitive adhesive suitable for contact with the skin or mucosa, e.g., dermatologically acceptable.

Active ingredient impermeable adhesives are typically coated onto the carrier or backing layer in liquid form. The liquid form of the adhesives are obtained either by dissolution or suspension of the adhesive components in a liquid vehicle or emulsion or by heating a thermoplastic adhesive above its melt temperature. The adhesive layer is then either dried by evaporation of the liquid vehicle or emulsion or hardened by cooling thermoplastic material below its melt temperature. Active ingredient impermeable adhesives are thus defined as being impermeable to the active ingredient when the adhesive layer is substantially dry or hardened.

Examples of suitable pressure sensitives for use in the present invention as the active ingredient impermeable adhesive layer include some natural rubber and synthetic rubber adhesives and cross-linkable laminating adhesives.

Examples of suitable natural rubber adhesives include R-1072 from B.F. Goodrich Co., No. 735 from C.L. Hathaway, and No. 5702 from Evans St. Clair. Examples of synthetic rubber adhesives include Jowatherm 270-00 and Jowatherm S-3202 from Jowat Corp. and 70-9416 from National Starch. Other suitable laminating adhesives include the Dow Corning laminating silicone adhesives and the Lord Corporation Tycel 7900 series laminating adhesives. The adhesives most impermeable to most active ingredients are cross-linkable laminating adhesives, which are well-known to those of ordinary skill in the art.

When utilizing pressure-sensitive adhesives, as the thickness of the adhesive layer affixing the backing layer to the carrier layer increases, the impermeability of the adhesive layer to the active ingredient also increases. To provide active ingredient impermeability to the adhesive layer, the thickness of the active ingredient impermeable adhesive layer 18 of FIG. 1 or 118 of FIG. 3 is that thickness that provides sufficient impermeability to the active ingredient (and if necessary, to the other components of the device with which the impermeable adhesive layer is in contact) so that the active ingredient does not seep out of the device as explained above. Typically, to obtain active ingredient impermeability, the impermeable adhesive layer joining the backing layer to the carrier layer will have a thickness between about two and about five mils, and preferably will have a thickness of about two mils.

Cross-linkable pressure-sensitive adhesives provide even greater impermeability of the adhesive layer to active agents and enhancers. By increasing the cross-link density of the adhesive layer, an even greater barrier to active agent diffusion is provided.

Returning to the structure of the devices shown in the embodiment of FIGS. 3 and 4, the width of the adhesive layer 118 extending peripherally beyond the carrier layer 112 about the entire periphery thereof coextensively with the backing layer 116 is that width which provides at least sufficient adhesion of the device to the skin or mucosa of the host in combination with the active ingredient permeable adhesive layer 114. Impermeability to the active ingredient (and, if necessary, to the other components of the device with which the adhesive layer is in contact) so that the active ingredient does not seep out of the device, increases as the width of the layer increases.

Suitable widths will vary depending upon the active ingredient and the degree of impermeability decreased, and range from 1/16 to 2 inches, and preferably, 1/8 to 1 inch. In most instances, the width will be from 1/4 to 1/2 inch depending on the specific use. The width need not be uniform and may vary around the perimeter of the device, e.g., to provide a specific geometric shape or to provide a tab for removal of a protective liner.

The devices of the present invention may also include an active ingredient permeable adhesive layer between the carrier layer and the skin or mucosa of the host, joining the device thereto. The active ingredient permeable adhesive layer is represented by layer 14 in FIGS. 1 and 2, layer 114 in FIGS. 3-6, layer 214 in FIGS. 7-9 and layer 314 in FIGS. 10-12. Certain embodiments utilize a second active ingredient permeable adhesive layer. For example, as shown in FIG. 2, active ingredient permeable adhesive layer 24 affixes rate-controlling polymer layer 22 to surface 15 of carrier layer 12. The device is then affixed to the skin or mucosa of the host by active ingredient permeable adhesive layer 14, which is applied to the surface of the rate-controlling polymer layer 22 opposite to carrier layer 12. Such a second active ingredient permeable adhesive layer is also represented by layer 124 in FIG. 5, layer 224 in FIG. 9 and layer 324 in FIG. 12.

The active ingredient permeable adhesive layer that joins the device to the skin or mucosa of the host is preferably dermatologically acceptable. Each active ingredient permeable adhesive layer is also preferably a pressure-sensitive adhesive. Any of the well-known, dermatologically acceptable, pressure-sensitive adhesives which permit drug migration therethrough can be used in the present invention.

Some suitable permeable adhesives include acrylic or methacrylic resins such as polymers of alcohol esters of acrylic or methacrylic acids and alcohols such as n-butanol, isopentanol, 2-methylbutanol, 1-methyl-butanol, 1-methylpentanol, 2-methylpentanol, 3-methylpentanol, 2-ethylbutanol, isooctanol, n-decanol, or n-dodecanol, alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butyl-acrylamide, itaconic acid, vinyl acetate, N-branched alkyl maleamic acids wherein the alkyl group has 10–24 carbon atoms, glycol diacrylates, or mixtures of these monomers; polyurethane elastomers; vinyl polymers such as polyvinyl alcohol, polyvinyl ethers, polyvinyl pyrrolidone, and polyvinyl acetate; urea formaldehyde resins; phenol formaldehyde resins, resorcinol formaldehyde resins; cellulose derivatives such as ethylcellulose, methylcellulose, nitrocellulose, cellulose acetate butyrate and carboxymethylcellulose; and natural gums such as guar, acacia, pectina, starch, destria, gelatin, casein, etc. Other suitable pressure-sensitive adhesives include polyisobutylene pressure sensitive adhesives, rubber pressure-sensitive adhesives and silicone pressure-sensitive adhesives. The adhesives may also be compounded with tackifiers and stabilizers as is well-known in the art.

Adhesives that are preferred for their active agent permeability include acrylic copolymer adhesives such as Avery Chemical Company's AS-351 HSX, preferably at a coating weight of between 25 and 35 g/m$^2$. This pressure-sensitive adhesive is a cross-linkable polymer which provides a permanently tacky film having a total solids content of about 52%, Brookfield viscosity (LVT/Spindle No. 4/12 RPM @ 25° C.) of from about 15,000 to 25,000 cps. at a weight per gallon of about 7.4 lbs. It can also be diluted with hexane or toluene to a desired solids and/or viscosity range, particularly for use in conventional coating equipment.

Other such adhesives that can also be used for these purposes include an acrylic pressure-sensitive adhesive sold by National Adhesives under the designation DUROTAK 80-1054. This adhesive has a solids content of 47.5%, a viscosity of 3,000 cps., and plasticity (Williams) of 2.9 mm. It is generally used with a solvent system including ethyl acetate, heptane, isopropyl alcohol and toluene. Another such adhesive is sold by Monsanto under the designation GELVA Multipolymer Emulsion 2484, and comprises a stable aqueous acrylic emulsion pressure-sensitive adhesive having a solids content of 59% and a viscosity of 1,500 to 2,300 cps. Examples of other acrylic adhesives include Gelva 788 and 733 from Monsanto, PS-41 from C. L.-Hathaway, Vr-0833 from H. B. Fuller, Adcot 73A207A from Morton Chemical, Nos. 80-2404, 80-1054, 72-9056 and 72-9399 from National Starch, Nos. E-2015, E-2067 and E-1960 from Rohm & Haas, M-6112; from Uniroyal, Inc. and Daratak 74 L from W. R. Grace. Suitable rubber adhesives include Durotak 36-6172 from National Starch and Morstik 118 from Morton Chemical. An example of a suitable silicone adhesive is X7-4502 from Dow Corning.

The active ingredient permeable adhesive layers preferably contain some of the active ingredient when the device is placed on the skin. This provides an initial active ingredient presence at the skin or mucosa and eliminates delay in absorption of the active ingredient or in topical application, if that is desired. Thus, the active ingredient is immediately available to the host. The initial active ingredient presence may be due to the migration through the adhesive layer or layers and, if present, rate-controlling layer, or to an amount of the active ingredient mixed in with the active ingredient permeable adhesive layer or layers or rate-controlling layer during manufacture. Thus, while either or both the active agent or active agent enhancer may be present in several of the laminate layers utilized, this may be the result of incorporation of the ingredients in only one of the layers, followed by migration of the ingredients to other layers.

The amount of the active agent or active agent enhancer present in the permeable adhesive layer or layers depends upon the initial drug presence desired, e.g., for a pulse dosage. For example, U.S. Pat. No. 4,031,894 discloses that 10–200 micrograms scopolamine base per cm$^2$ effective surface area is a suitable initial amount of active agent in the permeable adhesive layer.

The width (i.e., surface area) and thickness of the permeable adhesive layer for contact with the skin or mucosa is that width and thickness which provides sufficient permeability to the active agent or active agent enhancer and a suitable surface area to allow the dosage rate desired to the skin or mucosa. These widths and thicknesses are conventional in the art and therefore need not be discussed in detail here.

FIGS. 3–6 and 10–12 depict peripheral adhesive layers in direct contact and/or adjacent to the permeable adhesive layer. However, this is not necessary and there may be a gap between the peripheral adhesive layer and the permeable adhesive layer, if desired.

The thickness and shapes of the peripheral and permeable adhesive layers in the devices of the embodiments depicted in FIGS. 3–6 and 10–12 of the present invention need not be the same or correspond. This is a particular advantage to these embodiments of the invention in that the devices can be made to adhere to specific portions of the skin or mucosa by a primary means of the peripheral adhesive layers while not affecting the surface area of the permeable adhesive layer through which the active ingredient passes (i.e., the shape of the device can be varied without varying the surface area of the permeable adhesive layer which determines the amount of active agent delivered to the skin or mucosa).

With respect to the active ingredient carrier layers, such as carrier layer 12 of FIGS. 1–2, carrier layer 112 of FIGS. 3–5, carrier layer 212 of FIGS. 6–8 and carrier layer 312 of FIGS. 9–11, these layers are monolithic polymeric active ingredient carrier layers. Thus, in essence, these monolithic active ingredient carrier layers basically comprise a thermoplastic polymeric matrix which is admixed with the active agent or drug component or active agent enhancer, or both. Unlike the monolithic polymer matrix carrier layers of the prior art, which blend the active agent with a matrix polymer in a common solvent and then evaporate the solvent to form a plastic film, the carrier layers of the present invention are formed by blending a thermoplastic matrix polymer with the active agent at an elevated temperature above which the polymer softens and melts, at which temperature the polymer is molten and fluid. For purposes of this invention, this process is defined as melt-blending.

As is readily understood by those of ordinary skill in the art, the step of melt-blending requires the use of a thermoplastic polymer, that is, one that softens and melts when exposed to heat and then returns to its original condition when cooled. The melt-blending of the thermoplastic matrix polymer and the active agent is discussed in greater detail below.

Suitable thermoplastic matrix polymers for the carrier layer, particularly for amine-containing active agents such as nicotine, include the class of elastomeric resins which are polyether block amides, commercially designated by the trademark PEBAX. The structure of these polymers can be generally represented by the formula:

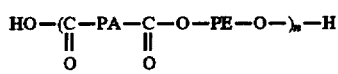

in which PA represents a rigid polyamide segment and PE represents a relatively soft polyether segment. Another class of suitable thermoplastic matrix polymers is the thermoplastic polyurethanes. Of this class, the polyether polyurethanes are preferred. These include such commercial polyurethane compositions such as Dow Chemical Company's PELLETHANE, including its 2363-80 AE grade thereof; K. J. Quin's Q-THANE; B. F. Goodrich's ESTANE; Mobay Chemical Company's TXIN; and others.

Suitable thermoplastic matrix polymers also include various polyesters, such as the copolymers of various cyclic polyesters including DuPont's HYTREL, including its 4056 grade thereof, and General Electric's LOMOD both- of which are copolymers of polyether prepolymers and polybutylene terephthalate and polyisobutylene terephthalate, respectively, as well as Eastman Chemical's PCCE. Other suitable polymers include ethylene methacrylic and acrylic acid copolymers. For example, ethylene methacrylic acid having the commercial designation NUCREL 699 is particularly suitable as a thermoplastic matrix polymer for estradiol.

As will be readily understood by those of ordinary skill in the art, the active agents suitable for use in the present invention must be heat stable at the melt temperature of the matrix polymer, and not react with the matrix polymer at this temperature. Active agents are defined as anything to be delivered topically to or through the skin. In general, the active agents must withstand exposure to temperatures in the range of about 170° C. to about 200° C. for incorporation into the resin matrix during the melt-blending process.

Active agents must have relatively good solubility in the polymer matrix, or can be solubilized in heat-resistant liquid carriers compatible with the polymer matrix prior to the melt-blending step, such as heat-resistant liquid plasticizers suitable for use in pharmaceutical skin contact compositions, which are well-known to those of ordinary skill in the art. Heat stability, for purposes of this invention, if an insubstantial degree of thermal breakdown of the material occurs within the temperature range of melt-blending over the time period required for melt-blending, generally a matter of several minutes. Active agents that are heat-sensitive but do not suffer rapid thermal degradation can be protected from heat and made suitable for use in the present invention by predispersion in the above-described heat resistant liquid carriers. Therefore, the definition of an active agent that is heat stable at the melt temperature of the matrix polymer includes active agents compatibilized or heat-stabilized by dispersion in a compatible heat-resistant liquid carrier prior to melt-blending with the matrix polymer.

The active agents may be, for example, systemic or topical drugs. Individual active agents or mixtures thereof, if desired, can be employed. Any drug which passes through the skin or mucosa can be employed for internal administration in the device of the invention, so long as the drug will pass through the permeable adhesive layer or layers present and is heat stable at the melt temperature of the matrix polymer.

Suitable systemic drugs for administration by the devices of the present invention include psychoactive agents such as nicotine, caffeine, mesocarb, mefexamide, cannabinols such as THC, and the like, sedatives such as diazepam, mepiridine, uldazepam, tybamate, metaclazepam, tetrabarbitol and the like, antidepressants such as amitryptyline, imipramine desipramine, nialamide, melitracen, isocarboxazid, and the like, anticonvulsants such as phenobarbitol, carbamazepine, methsuximide, 2-ethyl-2-phenylmalonamide (PEMA), phenytoin and the like, steroids such as progesterone, testosterone, pregnanediol, progestin, estradiol, analbolic steroids and the like, analgesics, including narcotic analgesics such as codeine, morphine, analorphine, demeral and the like, and analgesics such as acetaminophen, aspirin, alprazolam and the like, antimicrobial agents such as sulconazole, siccanin, silver sulfadiazine, bentiacide, and the like, tranquilizers such as meprobamate and the like, antineoplastic agents such as sulfosfamide, rufocromomycin and the like, and antibiotic agents such as tetracycline, penicillin, streptozcin and the like.

The quantity of active agent present in the thermoplastic matrix polymer carrier layer is that quantity sufficient to provide a pharmaceutically or physiologically effective dosage rate of the active agent to a host in need thereof. This quantity can be readily determined by those of ordinary skill in the art without undue experimentation as shown in the examples set forth below.

In general, the active agent will be present in the thermoplastic matrix polymer layer at levels between about 2% and about 10% by weight. When the active agent is nicotine, a nicotine concentration in the thermoplastic matrix polymer layer between about 4% and about 12% by weight is suitable, and a concentration between about 8% and about 10% by weight is preferred. A nicotine concentration of about 9% by weight is most preferred.

The devices of the present invention optionally include a rate-controlling polymer layer depicted as layer 22 in FIG. 2, layer 122 in FIG. 5, layer 22 in FIG. 9, and layer 322 in FIG. 12. The polymers suitable for use as the rate-controlling polymer layer are conventional in the art and need not be discussed in detail here. Some preferred materials include, for example, polyethylene, polypropylene, ethylene vinyl acetate copolymer (EVA), copolyesters (e.g., HYTREL) and polyurethanes. As will be discussed in greater detail hereinbelow, the active agent and thermoplastic matrix polymer can be melt-blended in an extruder and then formed into the carrier layer by extrusion. In accordance with this aspect of the invention, the most preferred embodiments of the invention incorporating a rate-controlling polymer layer omit the active agent permeable adhesive layer affixing the rate-controlling polymer layer to the carrier layer and instead co-extrude the two layers together.

The rate of permeation of the active agent through the rate-controlling polymer layer depends on factors such as the affinity of the active agent for the polymer layer, molecular size of the active agent, polymeric structure of the carrier layer and the thickness of the layer. Therefore, the appropriate rate-controlling polymeric material and its thickness depend on the active agent used and the desired rate of permeation. The selection of a polymer layer and its thickness provides a means, if desired, for controlling the dosage rate to the skin or mucosa.

As noted above, an enhancer to promote the penetration of the active agent through the skin may be included in either the carrier layer, rate-controlling polymer layer or the active agent permeable adhesive layers. The enhancer may be incorporated into these layers by solvent blending or, more preferably, by melt-blending by the same process utilized to incorporate the active agent into either the carrier layer or the rate-controlling polymer layer.

Suitable enhancers include those described in the above-cited U.S. Pat. No. 4,573,996, such as the following enhancers with a sufficiently high boiling point: monovalent, saturated and unsaturated aliphatic and cycloaliphatic alcohols having 6 to 12 carbon atoms such as cyclohexanol, lauryl alcohol and the like; aliphatic and cycloaliphatic hydrocarbons such as mineral oils; cycloaliphatic and aromatic aldehydes and ketones such as cyclohexanone; N,N-di (lower alkyl) acetamides such as N,N-diethyl acetamide, N,N-dimethyl acetamide, N-(2-hydroxyethyl) acetamide, and the like; aliphatic and cycloaliphatic esters such as isopropyl myristate and lauricidin; N,N-di (lower alkyl) sulfoxides such as decylmethyl sulfoxide; essential oils; nitrated aliphatic and cycloaliphatic hydrocarbons such as N-methyl-2-Pyrrolidone, Azone; salicylates, polyalkylene glycol silicates; aliphatic acids such as oleic acid and lauric acid, terpenes such as cineole, surfactants such as sodium lauryl sulfate, siloxanes such as hexamethyl siloxane; mixtures of the above materials; and the like.

When the active agent enhancer is to be melt-blended with the carrier layer, rate-controlling polymer layer or active agent permeable adhesive layer, the enhancer should be an active agent enhancer heat stable at the melt temperature of the carrier polymer, rate-controlling polymer or active agent permeable adhesive into which it is to be melt-blended. In general, the active agent enhancer should be heat stable at temperatures between about 170° C. and about 200° C. As with the active agents, the active agent enhancers can first be dispersed with a compatible heat-resistant liquid carrier to compatibilize the enhancer with the polymer or adhesive or to improve the heat resistance of the enhancer.

Examples of heat-resistant liquid carriers suitable for melt-blending with polymers or adhesives include polyethylene glycols, polypropylene glycols, polyester and polyether polyols, epoxidized linseed oils and simple liquid esters such as triethyl citrate, dicyclohexyl phthalate, diisodecyl adipate, and the like. The preferred liquid carrier is polyethylene glycol.

In a preferred embodiment, the device contains a protective liner attached to the device at the surfaces to be adhered to the skin or mucosa, namely the active agent permeable adhesive layer and, if present, the peripheral adhesive layer. The protective liner may be made of the same materials suitable for use in the backing layer as discussed above. Such material is preferably made removable or releasable from the adhesive layers by, for example, by conventional treatment with silicon, Teflon or other suitable coating on the surface thereof. The removal of the device from the protective liner may also be provided by mechanical treatment of the protective liner, e.g., by embossing the protective liner.

The protective liner, however, can comprise various layers, including paper or paper-containing layers or laminates; various thermoplastics, such as extruded polyolefins, such as polyethylene; various polyester films; foil liners; other such layers, including fabric layers, coated or laminated to various polymers, as well as extruded polyethylene, polyethylene terephthalate, various polyamides, and the like.

A particularly preferred embodiment of the protective liner of the present invention includes a laminate of an outer foil layer and an inner layer of plastic, such as polyethylene or the like, which is rendered releasable not only by means of a siliconized coating, but which also includes an embossed or roughened surface. Embossment of this surface can be accomplished by a number of conventional methods. In general, preparation of embossed surfacing can be accomplished by the use of male-female tooling, preferably enhanced by the application of heat. The principle intention of this embossment process is to roughen the surface or render it uneven so that less than the entire surface will be in physical contact with the corresponding adhesive layer.

The actual pattern of embossment carried out can vary, and in some instances may involve embossment of large contiguous areas of the protective liner. Preferably, approximately 30% of the surface of the protective liner will thus be embossed. The particular design of the embossment, such as the production of a grainy texture or the like, is a matter of choice within the parameters discussed above. The presence of the embossed surface on the inner surface of the protective liner is thus extremely significant in preventing the protective liner from sticking or adhering to the adhesive layer or layers, which would cause the liner to fail to properly separate from the adhesive layer or layers when it is desired to use the device of the present invention. This ease of operation is an important element in commercialization of these devices.

The selection of a particular protective liner will also depend upon other ultimate requirements of the particular device in question, including whether there is a desire for a transparent or opaque liner, etc.

It can thus be seen that although substantially the entire surface of the protective liner is in contact with the adhesive layer or layers, the seal provided to the adhesive layer or layers by the protective liner is "peelable" or releasable, by merely pulling apart the edge of the protective liner. At the same time, when this is done, the adhesive layer or layers for contact with the skin or mucosa remain in contact with the surface of the carrier layer and the peripherally extended backing area, if present, because of the coefficient of adhesion between the adhesives and these layers vis-a-vis the coefficient of adhesion between these adhesive layers and the coated surface of the protective liner.

The bottom layer of the embodiments depicted in FIGS. 7–12 should be flexible enough to generally follow the contour of the area of the host where the device is to be applied. On the other hand, it should have enough strength and substance so as to serve its function of carrying the active agent carrying members without wrinkling, etc. The actual material from which the bottom layer can be produced can therefore include a variety of different materials.

Some suitable materials for this layer include, for example, polyethylene, polypropylene, polyvinylidine chloride, polyethylene terephthalate, polyesters, polyamides, and others, as well as laminates of two or more of these layers with each other or one or more of these layers with additional layers such as foil, paper, various fabrics, etc., but in these cases, preferably with the polymer layer on the inside, i.e., in contact with and thereby carrying the active agent carrying members. Therefore, in a preferred aspect of these embodiments of the invention, the bottom layer is a laminate of an outer foil layer and an inner layer of plastic, such as polyethylene or the like.

The backing layers of the active agent carrying members are disposed onto the bottom layer by one of the above-mentioned acrylic, natural rubber or synthetic rubber pressure-sensitive adhesive. The adhesive layer thickness is controlled in the conventional manner to insure that the active agent carrying members preferentially adhere to the skin or mucosa of the host over the bottom layer.

The host to which an active agent is administered by means of the inventive device may be any host on which a drug or other active agent has the desired effect. The host may be, for example, a mammal such as a human being, or, for that matter, any warm-blooded or cold-blooded animal. The advantage of administering the active agent may be therapeutic or experimental. The device of this invention may also be used for any other advantageous purpose.

The various layers of the device of the present invention may be combined to form a laminate by methods conventional in the art. However, the present invention includes an inventive process for combining the active agent and a thermoplastic matrix polymer by melt-blending the two components, as well as an inventive process for combining polymer layers together by extrusion, preferably coextrusion.

The active agent and thermoplastic matrix polymer can be melt-blended using any art-recognized method for blending polymers with additives. Essentially, the thermoplastic matrix polymer is melt-blended with the active agent at a temperature above the softening point of the polymer using any conventional melt-blending apparatus including extruders, calenders, kneaders, sigma bladed mixers such as Brabender-type mixers, Banbury-type mixers and the like, preferably at a temperature between about 170° C. and about 200° C.

The active agent can also be melt-blended with the rate-controlling polymer by the above-described method. In addition, the active agent enhancer can also be melt-blended with either the thermoplastic matrix polymer or the rate-controlling polymer by the above-described method.

The carrier layers for the devices of the present invention can be formed directly from the resulting blend or die-cut from films formed therefrom. As such, the blends of thermoplastic matrix polymer and active agent of the present invention can be directly extruded, calendered, compression-molded, injection-molded, thermoformed or otherwise cast, by conventional solvent-free methods well-known to those of ordinary skill in the art. Alternatively, the blend of active agent and thermoplastic matrix polymer can first be formed by extrusion into pellets for storage, which pellets can subsequently be formed into the carrier layer by any of the above-mentioned forming methods.

The carrier layers of the present invention are preferably formed in compounder-extruders in which the active agent and thermoplastic matrix polymer can be melt-blended and the resulting melt-blend extruded into the above-mentioned pellets, or into a film from which carrier layers may be formed, or into the actual carrier layers. The entire process is carried out without dissolving the polymer, the active agent, or the active agent and polymer blend in a solvent for the polymer or active agent other than the optional compatible heat-resistant liquid carrier.

The monolithic carrier layer, once formed, can be immediately die-cut and combined on one surface with the backing layer. Alternatively, the layers can be combined prior to die-cutting. The backing layer is either laminated to the carrier layer by an adhesive layer, or by extruding the backing layer and carrier layer together. As will be readily understood by those of ordinary skill in the art, when the backing layer and carrier layer are extruded together without an active agent impermeable adhesive layer, then it is critical that the backing layer be formed from an active agent impermeable material.

The adhesive layer providing a means for affixing the device to the skin or mucosa for the host is applied to either the carrier layer and the extruded peripheral area of the backing layer, if present. If a rate-controlling polymer layer is affixed to the carrier layer, then any adhesive layer to be affixed to the carrier layer is applied to the rate-controlling polymer layer instead. Such adhesive layers can be applied either before or after the carrier layer and backing layer are laminated together.

Die-cutting, whenever mentioned herein, is carried out by processes well-known in the laminating art.

As noted above, certain embodiments include a rate-controlling polymer layer affixed to the carrier layer on the surface to be applied to the skin or mucosa of a host. This polymer layer is either adhered to the carrier layer by an active agent permeable adhesive layer, or, this layer can also be extruded with the carrier layer, alone, or with the backing layer. As is well understood to those of ordinary skill in the polymer forming art, layers of the same or different polymers are conventionally extruded together. Two or more of the carrier layer, backing layer and rate-controlling polymer layer can be coextruded together in a single step. When all three layers are coextruded, the only adhesive layer required will adhere the rate-controlling polymer layer, and thus the laminate, to the skin or mucosa of the host.

The device, once formed, may be kept sealed in an air-tight pouch prior to use. The device of the present invention is used in the same manner as those devices which are conventional in the prior art. In most instances, the releasable protective liner attached to the skin-side surface of the adhesive layer or layers of the device for contact with the skin or mucosa of the host is removed and such surface of the adhesive layer or layers is applied to the desired area of the skin or mucosa.

The following non-limiting examples set forth hereinbelow illustrate certain aspects of the invention, but are not meant in any way to restrict the effective scope of the invention. All parts and percentages are by weight unless otherwise noted, and all temperatures are in degrees Celsius.

EXAMPLES

Example 1

A mixture of 5.5 lb. of PEBAX-4033 polyether-polyamide block copolymer resin was melt-blended with 227 g of nicotine in a Werner-Pfleiderer Model ZSK-30 30 mm twin screw compounder extruder. The two components were melt-blended at 170° C. and extruded into pellets. The nicotine content of the pellets was determined to be 8.20% by methanol extraction.

A film having an average thickness of 9.6 mil was pressed out of the pellets using a Carver laboratory press at a pressure of 1500 psi and a melt temperature of 350° F. 10 cm discs were die-cut from the pressed-out film having an average thickness of 9.6 mil and an average weight of 242.3 mg.

Mono Discs were formed from the PEBAX-nicotine discs by affixing the 10 cm$^2$ PEBAX discs to 10 cm$^2$ SARAN/HYTREL occlusive film discs 1.5 mil thick with a 3.1 mil thick layer of Gelva 737 (Monsanto) acrylic pressure-sensitive adhesive. The opposite side of the disc was then coated with a 1.7 mil thick layer of Gelva 737, which is a skin contact pressure-sensitive adhesive. The adhesive was then covered with a release liner.

Double discs were also prepared as in FIG. 3–4 utilizing a 20 cm$^2$, 1.5 mil thick SARAN/HYTREL occlusive film as the backing layer 116, which was coated with a 3.1 mil thick layer of Gelva 737 acrylic pressure-sensitive adhesive, serving as the adhesive layer 118. The 10 cm$^2$ PEBAX-nicotine disc served as the carrier layer 112. A 1.7 mil thick coating of Gelva 737 pressure-sensitive adhesive served as the adhesive layer 114. The skin contact adhesive was also protected with a release liner.

The nicotine content of these two types of patches was determined by methanol extraction, with a NICOTINELL-TTS 20 (Ciba-Geigy) patch measured as a control. The NICOTINELL-TTS 20 patch is a laminate of 0.5 mil of an occlusive film to a 6.0 mil non-woven cellulose layer with a 4.5 mil acrylic pressure-sensitive adhesive. The non-woven cellulose layer is impregnated with nicotine. The opposite side of the cellulose layer is then coated with an 8.5 mil layer of a cross-linked acrylic skin contact pressure-sensitive adhesive, which is then covered with a release liner. The three patches were extracted in 40 mL methanol for 16 hours at room temperature and subsequently sonicated for ½ hour. Sonication is an action of ultra sound waves which generate high energy vibrations within a polar media such as water or methanol causing a rapid dissolution and disintegration of submerged materials.

Both the mono disc and double disc patches were determined by High Performance Liquid Chromatography (HPLC) to contain 18 mg of nicotine per 10 cm² patch. By the same test, the NICOTINELL-TTS 20 patch was determined to have a nicotine content of 35 mg.

Figure 13:
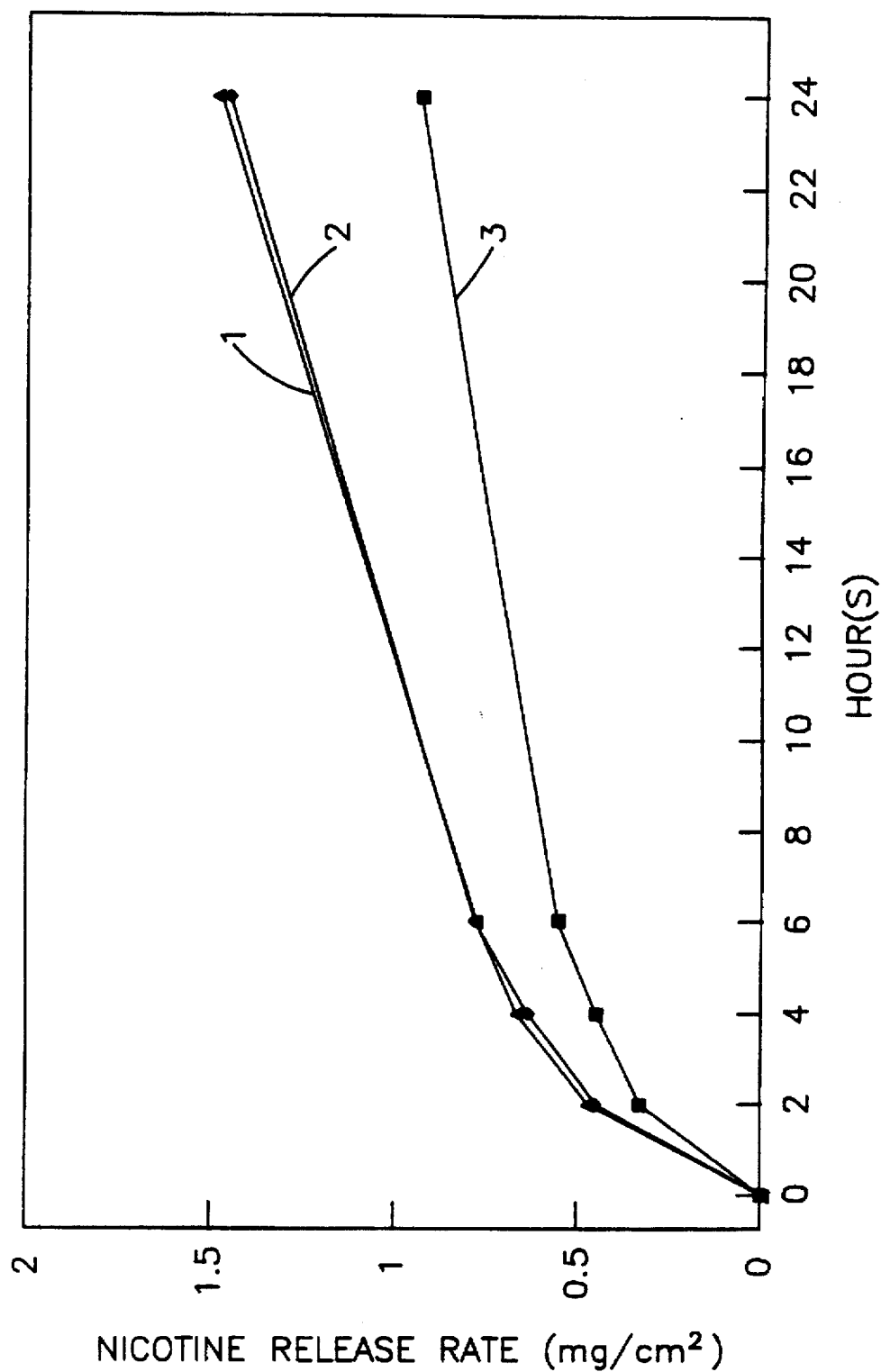
FIG. 13 shows the nicotine release rate of two devices prepared in accordance with separate embodiments of the present invention compared to a control device.

The nicotine release of the three patches was tested by a standardized testing method. Each of the three patches was attached to the bottom of a 250 mL beaker by means of double-sided adhesive tape in such a manner that the skin-contact side of the patch was facing upwards. 100 mL of water at room temperature was added to each beaker, the tops were sealed and the test starting time was recorded. At 2 hours, 4 hours, 6 hours and 24 hours, the water in the beakers was stirred for 2 minutes and a 2–3 mL sample was withdrawn from each beaker for analysis by HPLC. The concentration of the nicotine of the water was then determined using calibration standards, thus providing the drug release kinetics. The results are presented in Table I and FIG. 13. The results demonstrate that both the mono disc 1 and double disc 2 deliver nicotine transdermally at the same rate, and at a slightly greater rate than the control 3.

TABLE I

|  | Mono Disc | Double Disc | Nicotinell TTS 20 |
|---|---|---|---|
| Patch size | | | |
| Inner Disc | 10 cm² | 10 cm² | — |
| Outer Disc | — | 20 cm² | 20 cm² |
| Nicotine Content | 18.0 mg | 18.0 mg | 35.0 mg |
| Release Rate - (mg/cm²) | | | |
| 6 hrs. | 0.78 | 0.78 | 0.53 |
| 24 hrs. | 1.53 | 1.53 | 0.95 |
| Diffusion Rate - (mg/cm²) | | | |
| 6 hrs. | 2.01 | 2.01 | 1.56 |
| 24 hrs. | 3.16 | 3.16 | 2.78 |

The diffusion kinetics of nicotine from the three types of patches through a skin substitute was also measured using the Franz Diffusion Cell Method. In this method, an excised human or animal skin was overlayed with a transdermal patch in such a way that the adhesive side of the patch was in contact with the skin. This patch/skin lamination was then mounted onto a Franz Diffusion Cell on top of the lower, or receiving, chamber of the cell, which was filled with isotonic saline at pH 7.4. This saline solution contacts the skin at the top of the chamber. The temperature of the isotonic solution was maintained at 37° C. by thermostatically controlled water circulation through a jacket surrounding the receiving chamber. Homogeneous distribution of temperature was achieved by a small magnetic stirrer. Thus, the skin was held under conditions approximating the living state.

At 2 hours, 4 hours, 6 hours and 24 hours, 1 to 2 mL of the saline solution was withdrawn from the receiving chamber and analyzed by HPLC. The drug concentration in the saline solution sample was calculated using calibration standards and the drug permeation kinetic profile through the skin was thus obtained.

Figure 14:
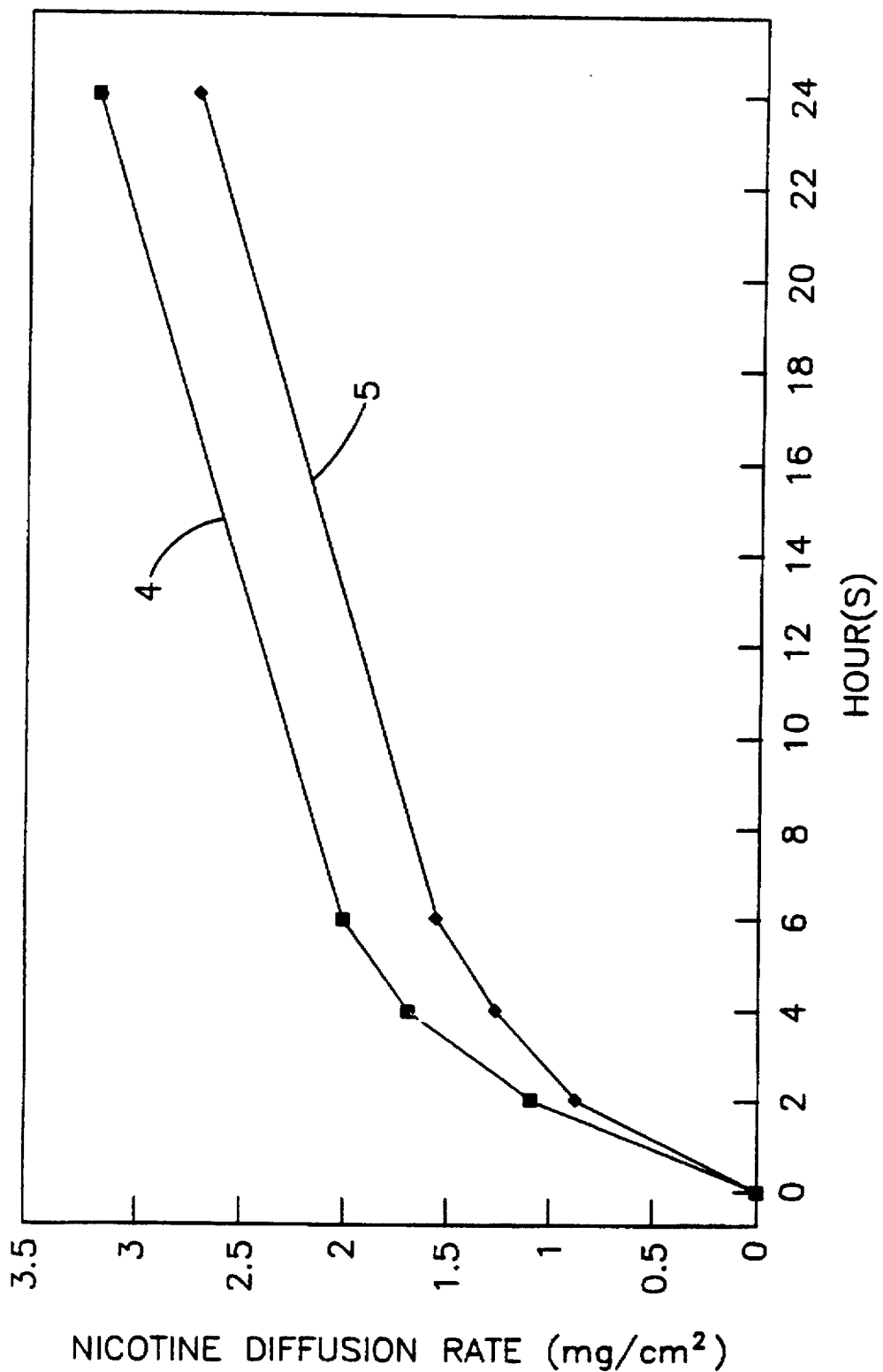
FIG. 14 shows the nicotine diffusion rate of two devices prepared in accordance with separate embodiments of the present invention compared to a control device.

The skin substitute utilized in Example 1 was porcine xenograft (E-Z Derm, from Bioplasty, Inc., St. Paul, Minn.). The results are presented in Table I and FIG. 14. Again, the test results demonstrate that both the mono disc and double disc deliver nicotine transdermally at virtually the identical rate 4, and at a slightly greater rate than the control 5.

Example 2

Figure 15:
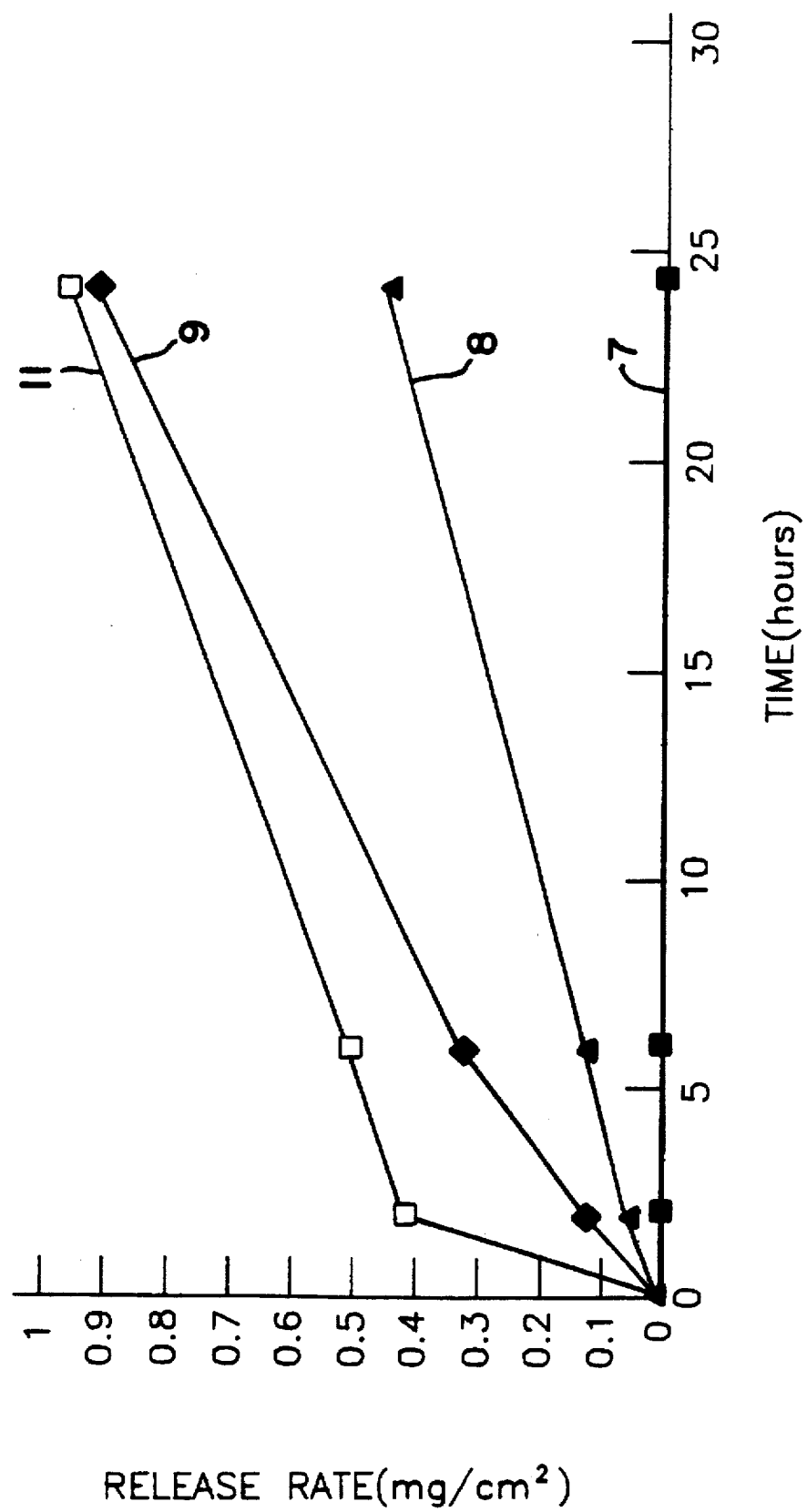
FIG. 15 shows the nicotine release rate of three devices prepared in accordance with the invention.

Mono disc patches containing rate-controlling polymer layers were prepared as in FIG. 2 by affixing the 10 cm² PEBAX discs of Example 1 to a 1.5 mil SARAN/HYTREL occlusive film with a 1.8 mil layer of Gelva 737 acrylic pressure-sensitive adhesive. The opposite side of the PEBAX disc was then coated with a 1.8 mil layer of Gelva 737 adhesive to which a 1.0 mil rate-controlling polymer layer was laminated. A 1.8 mil layer of Gelva 737 was then added to the opposite side of the rate-controlling polymer layer, which adhesive layer was then covered with a release liner. Patches were prepared with three different rate-controlling polymeric layers: Hytrel 4056, ethylene vinyl acetate (EVA) and SURLYN 1702 ionomer resin. A first control patch was prepared without a rate-controlling polymeric layer. A NICOTINELL-TTS 20 patch was utilized as a second control. The five patches were then analyzed for their release rates of nicotine by the test described in Example 1 in which each patch was attached to the bottom of a 250 mL beaker by double-sided adhesive tape with the skin-contact side of the patch facing upwards. The test and results are presented in Table II and FIG. 15. FIG. 15 depicts the release rate with time for patches with rate-controlling polymer layers of SURLYN 1702 7, EVA 8 and HYTREL 4056 9, compared to the NICOTINELL-TTS 20 control 11.

TABLE II

| Type of Rate Controlling Polymeric Layer | Release Rate mg/cm² After 24 Hours |
|---|---|
| None | 1.53 |
| 1 mil Hytrel 4056 | 0.87 |
| 1 mil EVA | 0.42 |
| 1 mil SURLYN 1702 | 0.00 |
| NICOTINELL-TTS 20 | 0.95 |

The most permeable rate-controlling polymer layer was the Hytrel 4056. The patch containing this rate-controlling polymer layer demonstrated a release rate comparable to the NICOTINELL-TTS 20 patch. The release rate for the patch with the Hytrel 4056 layer at 24 hours was 0.87 mg/cm², compared to 0.95 mg/cm² for NICOTINELL-TTS 20. These values may be considered to be the same within experimental error. EVA showed the slowest permeability, while Surlyn proved to be a very good barrier for nicotine.

In summary, this example demonstrates that a mono disc patch with a rate-controlling polymeric layer of 1.0 mil Hytrel 4056 delivers nicotine transdermally at practically the same rate as NICOTINELL-TTS 20.

Example 3

Mono disc patches containing different skin contact pressure-sensitive adhesives were prepared as in FIG. 1 by affixing the 10 cm² PEBAX disc of Example 1 to a 1.5 mil 10 cm² SARAN/HYTREL occlusive film disc with a 1.8 mil layer of Gelva 737. The opposite side of the PEBAX disc was then coated with a 1.8 mil layer of skin contact pressure-sensitive adhesive and covered with release liner. Patches were prepared with three different skin contact pressure-sensitive adhesives: Gelva 737, Durotak 36-6172 (National Starch and Chemical, Bridgewater, N.J.) and Morstik 118 (Morton International, Chicago, Ill.). The patches were then analyzed for their release rate of nicotine by the test described in Examples 1 and 2 in which each patch was attached to the bottom of a 250 mL beaker by double-sided adhesive tape with the skin-contact side of the patch facing upwards. The release kinetics results are depicted in Table III.

TABLE III

| Skin Contact Pressure-sensitive Adhesive | Release Rate After 24 Hours mg/cm$^2$ |
| --- | --- |
| NICOTINELL-TTS 20 | 0.95 |
| Gelva 737 | 1.53 |
| Durotak 36-6172 | 1.40 |
| Morstik-118 | 1.13 |

The results in Table III illustrate that the release rate of nicotine can be controlled by the selection of adhesive. With Morstik 118, the release kinetics are virtually the same as for NICOTINELL-TTS 20. Thus, it has been demonstrated that the skin contact pressure-sensitive adhesive controls the release rate of nicotine from the carrier polymer matrix.

Example 4

PEBAX-nicotine pellets were prepared as in Example 1 and then cast extruded into an 8.0 mil film on a carrier web. A 1.0 mil HYTREL 4033 film was cast extruded and heat laminated to the PEBAX film. A 1.0 mil MYLAR polyester occlusive layer was adhesive laminated to the opposite surface of the PEBAX film using 1.0 mil of GELVA 737 bonding adhesive. A 1.8 mil film of GELVA 737 skin contact adhesive was then transfer coated to the underside of the rate-controlling polymer layer. The film laminate was then die-cut into 20 cm$^2$ mono discs. Comparative analytic testing was then performed on these discs and reference patches from two different manufacturers. The reference patches were 10 cm$^2$ and 15 cm$^2$ NICODERM™ Nicotine patches (Marion Merrell Dow) and 10 cm$^2$ and 30 cm$^2$ HABITROL™ Nicotine patches (Basel Pharmaceuticals Division of Ciba-Geigy).

The nicotine content of the patches was determined by extracting the patches in HPLC grade methanol. The nicotine content was then quantitatively determined by analyzing the extracts using HPLC. The dissolution kinetics analysis was performed according to United States Pharmacopeia, Method USP XXII (724) No. 3, Paddle over Disc. The nicotine was quantified by HPLC. Franz Diffusion Cell Tests were performed at 37° C. using excised skin from a hairless guinea pig. Extracts were sampled after 24 hours and quantified on HPLC. The purity of the nicotine contained in the extruded PEBAX film was determined by extraction in HPLC grade methanol and acetonitrile. Three different analytical methods were used to determine if any impurities or degradation products were present in the PEBAX film, gas chromatography, HPLC and UV-VIS spectrophotometry. The GC and HPLC chromatograms were compared to GC and HPLC chromatograms of 99% pure, free base nicotine for the detection of additional peaks. The absorption bands of the UV-VIS spectra were also compared between the extract and 99% pure, free base nicotine.

The PEBAX nicotine patches were packaged in pouches classified as Category A according to USP standards, USP XXII (671). Two storage conditions were chosen, ambient temperature and relative humidity, and 40° C. and ambient relative humidity. The stability program was established for 26 weeks with interval testing performed at 4, 8, 13 and 26 week intervals. At each time interval, the dissolution kinetics and nicotine content procedures are performed.

The results of the nicotine content, dissolution testing, and Franz Diffusion Cell Testing are presented in Table IV. The PEBAX purity results are shown in Table V. With respect to the stability study of the PEBAX nicotine patch, as of Jan. 20, 1992, 4 and 8 week interval testing has been performed, and the results are shown in Table VI.

TABLE IV

| CONTENT OF NICOTINE | | |
| --- | --- | --- |
| Patch Description | Patch Area | Nicotine |
| Mono Disc | 20 cm$^2$ | 39.5 mg |
| NICODERM ™ Patch | 15 cm$^2$ | 78.0 mg |
| HABITROL ™ Patch | 20 cm$^2$ | 35.0 mg |

| DISSOLUTION RESULTS | | |
| --- | --- | --- |
| Patch Description | 6 Hours | 24 Hours |
| Mono Disc | 1.47 mg/cm$^2$ | 2.09 mg/cm$^2$ |
| NICODERM ™ (10 cm$^2$ Fragment) | 0.97 mg/cm$^2$ | 1.60 mg/cm$^2$ |
| HABITROL ™ (10 cm$^2$ Fragment) | 1.71 mg/cm$^2$ | 3.07 mg/cm$^2$ |

| FRANZ DIFFUSION CELL RESULTS | | |
| --- | --- | --- |
| | Nicotine In-Vitro Diffusion Rate After 24 Hours | |
| Patch Description | mg/Exposed Area | mg/cm$^2$ |
| Mono Disc | 2.2 | 0.58 |
| NICODERM ™ | 3.1 | 0.82 |
| HABITROL ™ | 2.2 | 0.59 |

TABLE V

| PURITY OF NICOTINE EXTRUDED FILM | |
| --- | --- |
| Analytical Method | Impurity/Degredation Peaks Detected |
| Gas Chromatography | None |
| High Performance Liquid Chromatography | None |
| UV-VIS Spectrophotometry | None |

TABLE VI

| STABILITY STUDY RESULTS | | | | | |
| --- | --- | --- | --- | --- | --- |
| ANALYT- ICAL TEST | START VALUE | ROOM TEMPERATURE | | 40° CELSIUS | |
| | | 4 WEEKS | 8 WEEKS | 4 WEEKS | 8 WEEKS |
| Dissolution Kinetics For 24 Hours [mg/cm$^2$] | 2.09 | 2.05 | 2.02 | 2.07 | 1.88 |
| Nicotine Content Per Patch | 39.5 | 39.3 | 37.7 | 39.4 | 35.8 |

TABLE VI-continued

STABILITY STUDY RESULTS

| ANALYT-ICAL TEST [mg] | START VALUE | ROOM TEMPERATURE | | 40° CELSIUS | |
|---|---|---|---|---|---|
| | | 4 WEEKS | 8 WEEKS | 4 WEEKS | 8 WEEKS |

The 15 cm$^2$ NICODERM™ patch and the 20 cm$^2$ HABITROL™ patch have the same published in vivo delivery rate of nicotine, 14 mg/day, yet the nicotine content is very different. Delivery rate therefore does not directly relate to nicotine content. Consequently, the in vivo delivery rate of the PEBAX patch cannot be calculated based solely on its nicotine content.

The exposed area of the patch for both dissolution testing and Franz Diffusion Cell Testing was die-cut from the center of NICODERM™ and HABITROL™ patches. The release rate in water shows significant differences among the three patches. Because the in vivo delivery rate is known to be 14 mg/day for both the NICODERM™ and HABITROL™ patches, this shows that no correlation may be drawn between water release rate and the in vivo delivery rate for the PEBAX nicotine patch.

With respect to the Franz Diffusion Cell results, the PEBAX nicotine patch shows identical percutaneous absorption through hairless guinea pig skin compared to the NICODERM™ and HABITROL™ patches. Because NICODERM™ and HABITROL™ patches exhibit identical in vivo delivery rates, one can safely project the in vivo delivery rate of the PEBAX patch. Calculated delivery rates for the three common standard sizes of nicotine patches are shown in Table VII.

TABLE VII

CALCULATED NICOTINE IN-VITRO DIFFUSION RATES FOR VARIOUS PATCH SIZES

| PATCH DESCRIPTION | IN-VIVO DELIVERY RATE [MG/DAY] | PATCH SIZE [CM$^2$] | IN-VITRO DELIVERY RATE [MG/DAY] |
|---|---|---|---|
| Mono Disc | 7 Projected | 10 | 6.0 |
| | 14 Projected | 20 | 12.0 |
| | 21 Projected | 30 | 18.0 |
| NICODERM ™ | 7 Known | 7 | 6.0 |
| | 14 Known | 15 | 12.0 |
| | 21 Known | 22 | 18.0 |
| HABITROL ™ | 7 Known | 10 | 6.0 |
| | 14 Known | 20 | 12.0 |
| | 21 Known | 30 | 18.0 |

With reference to the purity results of Table V, these results demonstrate that the extrusion process does not in any way degrade the nicotine or introduce impurities into the extruded PEBAX-nicotine matrix film. The stability study results of Table VI prove that the PEBAX-nicotine transdermal system is stable over time in varying storage conditions.

The PEBAX-nicotine transdermal system of the present invention clearly shows very similar release characteristics to other reference nicotine transdermal systems. Specifically, the in vitro release characteristic through guinea pig skin of the PEBAX-nicotine patch matches those of the reference patches very closely. The innovative physical structure and simplified construction of the PEBAX-nicotine transdermal system makes this system stand out from the other commercial nicotine patches by achieving substantial savings in manufacturing costs.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A process for assembling a device for the controlled release of an active agent to the skin or mucosa of a host, which process includes the steps of:
   (a) melt-blending at a temperature between about 170° C. and about 200° C. a thermoplastic matrix polymer having a melt temperature between about 170° C. and about 200° C. and selected from the group consisting of polyether block amides, ethylene methacrylic acid copolymers, ethylene acrylic acid copolymers, copolymers of polyether prepolymers with polybutylene terephthalate, copolymers of polyether prepolymers with polyisobutylene terephthalate and polyether polyurethanes, with an active ingredient that is heat stable at the melt temperature of said matrix polymer, so that a melt-blend of said active ingredient and said thermoplastic matrix polymer is formed, wherein said active ingredient is selected from the group consisting of active agents, active agent enhancers and mixtures thereof;
   (b) providing an active ingredient impermeable backing layer having an inner surface and an outer surface and extruding said melt-blend directly onto said inner surface of said backing layer so that said melt-blend is formed into a carrier layer having opposing first and second surfaces, wherein said second surface is directly laminated to said inner surface of said backing layer without an adhesive layer therebetween, so that said active ingredient cannot permeate from said second surface of said carrier layer to said outer surface of said backing layer; and
   (c) providing said laminate with means for securing said laminate to said skin or mucosa of said host so that said active ingredient is controllably released from said first surface of said carrier layer thereto.

2. The process of claim 1, wherein said step of providing said laminate with means for securing said laminate to said skin or mucosa of said host comprises the step of applying to said laminate an adhesive layer adapted to adhere said first surface of said carrier layer to said skin or mucosa of said host.

3. The process of claim 1, wherein said extruding step comprises the step of extruding said melt-blend directly onto said inner surface of said backing layer so that the surface area of said backing layer extends peripherally beyond said carrier layer about the entire periphery thereof so as to create an extended peripheral area of said backing layer, and said step of providing said laminate with means for securing said first surface of said carrier layer to said skin or mucosa of said host comprises the step of adapting said inner surface of said extended peripheral area of said backing layer to adhere to said skin or mucosa of said host so that said laminate firmly adheres thereto.

4. The process of claim 3, wherein said adapting step comprises coating said inner surface of said extended peripheral area of said backing layer with an adhesive layer adapted to adhere said backing layer to said skin or mucosa of said host.

5. The process of claim 3, wherein said step of providing said laminate with means for securing said laminate to said skin or mucosa of said host further comprises the step of coating said first surface of said carrier layer with an active ingredient permeable adhesive layer.

6. The process of claim 1, further comprising the step of affixing to said first surface of said carrier layer means for controlling the rate at which said active ingredient is released from said first surface of said carrier layer to said skin or mucosa of said host.

7. The process of claim 6, wherein said affixing step comprises coating said first surface of said carrier layer with an active agent permeable adhesive layer capable of controlling said rate at which said active ingredient is released from said first surface of said carrier layer to said skin or mucosa of said host.

8. The process of claim 6, wherein said affixing step comprises laminating a rate-controlling polymer layer to said first surface of said carrier layer.

9. The process of claim 8, wherein said step of providing said laminate with means for securing said laminate to said skin or mucosa of said host comprises coating said rate-controlling polymer layer on the surface opposite said carrier layer with an active ingredient permeable adhesive layer.

10. The process of claim 1, further comprising the steps of:
 (a) providing a removable liner layer having a first surface and a second surface, wherein said first surface of said liner layer is a releasable surface;
 (b) providing a bottom layer having a first surface and a second surface;
 (c) disposing a plurality of said laminates between said first surface of said bottom layer and said first surface of said liner layer, wherein said backing layer of each of said laminate is affixed to said first surface of said bottom layer and said means for securing each of said laminate to said skin or mucosa of said host is affixed to said liner layer; and
 (d) releasably heat sealing said first surface of said liner layer to said first surface of said bottom layer at least at a location between at least two laminates so as to physically separate said laminates prior to removal of said removable liner layer from said bottom layer, whereby removal of said liner layer eliminates said heat seal.

11. The process of claim 10, wherein said backing layer of each of said laminates are affixed to said first surface of said bottom layer by an adhesive layer having a coefficient of adhesion less than the coefficient of adhesion of said means for securing said laminate to said skin or mucosa of said host of each of said laminate.

12. The process of claim 1, wherein said backing layer comprises one or more layers of an occlusive material, wherein each layer of material is independently selected from the group consisting of cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride, paper, cloth and aluminum foil.

13. The process of claim 12, wherein each layer of material is independently selected from the group consisting of polyethylene, polypropylene, polyvinyl chloride, polyvinylidene chloride and polyethylene terephthalate.

14. The process of claim 1, wherein said adhesive layer adapted to adhere said laminate to said skin or mucosa of said host comprises a pressure-sensitive adhesive material selected from the group consisting of polyisobutylene adhesives, silicone adhesives, acrylic adhesives and synthetic rubber adhesives.

15. The process of claim 14, wherein said acrylic pressure-sensitive adhesive comprises a polymer of alcohol esters of acrylic or methacrylic acid.

16. The process of claim 15, wherein said esters of polyacrylic acid and polymethacrylic acid are esters of alcohols selected from the group consisting of N-butanol, isopentanol, 2-methylbutanol, 1-methylbutanol, 1-methylpentanol, 2-methylpentanol, 3-methylpentanol, 2-ethylbutanol, isooctanol, n-decanol and n-dodecanol.

17. The process of claim 16, wherein said esters of polyacrylic acid and polymethacrylic acid are copolymerized with one or more ethylenically unsaturated monomers selected from the group consisting of acrylic acid, methacrylic acid, acrylamide, methacrylamide, N-alkoxymethyl acrylamide, N-alkoxymethyl methacrylamide, N-t-butylacrylamide, itaconic acid, vinyl acetate, N-branched alkyl malemic acid with alkyl groups from 10 to 24 carbon atoms and glycol diacrylates.

18. The process of claim 2, wherein said active ingredient permeable adhesive layer comprises a dermatologically acceptable pressure-sensitive adhesive selected from the group consisting of polyurethane elastomers, polyvinyl alcohol, polyvinyl ethers, polyvinyl pyrrolidone, polyvinyl acetate, urea formaldehyde resins, phenol formaldehyde resins, resorcinol formaldehyde resins, ethyl cellulose, methyl cellulose, nitrocellulose, cellulose acetate butyrate, carboxymethyl cellulose, guar gum, acacia gum, pectina gum, destria gum, gelatin and casein.

19. The process of claim 1, wherein said active ingredient comprises an active agent selected from the group consisting of psychoactive agents selected from the group consisting of nicotine, caffeine, mesocarb, mefexamide and cannabinols; sedatives selected from the group consisting of diazepam, mepiridine, uldazepam, tybamate, metaclazepam and tetrabarbitol; antidepressants selected from the group consisting of amitryptyline, imipramine, desipramine, nialamide, melitracen and isocarboxazid; anticonvulsants selected from the group consisting of phenobarbitol, carbamazepine, methsuximide, 2-ethyl-2-phenylmalonamide and phenytoin; steroids selected from the group consisting of progesterone, testosterone, pregnanediol, progestin and estradiol; narcotic analgesics selected from the group consisting of codeine, morphine, analorphine and demeral; analgesies selected from the group consisting of acetaminophen, aspirin and alprazolam; antimicrobial agents selected from the group consisting of sulconazole, siccamin, silver sulfadiazene and bentiacide, tranquilizers; antineoplastic agents selected from the group consisting of sulfosamide and rufocromomycin; and antibiotic agents selected from the group consisting of tetracycline, penicillin and streptozocin.

20. The process of claim 19, wherein said active agent comprises nicotine.

21. The process of claim 8, wherein said rate-controlling polymer layer comprises a material selected from the group consisting of polypropylene, polyethylene, ethylene vinyl acetate, polyether polyurethanes, ethylene methacrylic acid copolymers, ethylene acrylic acid copolymers, polyether block amides, and copolymers of polyether prepolymers and polybutylene terephthalate and polyisobutylene terephthalate.

22. The process of claim 10, wherein said releasable surface comprises a siliconized coating.

23. The process of claim 10, wherein said liner layer comprises one or more layers, wherein each layer is independently selected from the group consisting of paper, thermoplastic polymers and metal foils.

24. The process of claim 10, wherein said bottom layer comprises one or more polymeric materials selected from the group consisting of polyethylene, polypropylene, polyvinylidene chloride, polyethylene terphthalate, polyesters and polyamides.

25. The laminate of claim 1, wherein said active agent enhancer is selected from the group consisting of monovalent, saturated and unsaturated aliphatic and cycloaliphatic alcohols having 6 to 12 carbon atoms, aliphatic and cycloaliphatic hydrocarbons, cycloaliphatic and aromatic aldehydes and ketones, N,N-dialkyl acetamides, aliphatic and cycloaliphatic esters, N,N-dialkyl sulfoxides, essential oils, nitrated aliphatic and cycloaliphatic hydrocarbons, salicylates, polyalkylene glycol silicates, aliphatic acids, terpenes, surfactants and siloxanes.

26. The process of claim 25, wherein said active agent enhancer comprises mineral oil.

27. The process of claim 8, further comprising the step of melt-blending said rate-controlling polymer layer with an active agent enhancer to promote the penetration of said active agent through said skin or mucosa of said host, prior to laminating said rate-controlling polymer layer to said first surface of said carrier layer, wherein said active agent enhancer is heat stable at a melt temperature between about 170° C. and about 200° C., so that a melt-blend of said active agent enhancer and said thermoplastic matrix polymer is formed.

28. The process of claim 27, wherein said active agent enhancer is selected from the group consisting of monovalent, saturated and unsaturated aliphatic and cycloaliphatic alcohols having 6 to 12 carbon atoms, aliphatic and cycloaliphatic hydrocarbons, cycloaliphatic and aromatic aldehydes and ketones, N,N-dialkyl acetamides, aliphatic and cycloaliphatic esters, N,N-dialkyl sulfoxides, essential oils, nitrated aliphatic and cycloaliphatic hydrocarbons, salicylates, polyalkylene glycol silicates, aliphatic acids, terpenes, surfactants and siloxanes.

29. The process of claim 27, wherein said active agent enhancer comprises mineral oil.

30. The process of claim 9, further comprising the step of melt-blending said active ingredient permeable adhesive with an active agent enhancer to promote the penetration of said active agent through said skin or mucosa of said host, prior to coating said rate-controlling polymer layer on said surface opposite said carrier layer with said adhesive, wherein said active agent enhancer is heat stable at a melt temperature between about 170° C. and about 200° C., so that a melt-blend of said active agent enhancer and said adhesive is formed.

31. The process of claim 30, wherein said active agent enhancer is selected from the group consisting of monovalent, saturated and unsaturated aliphatic and cycloaliphatic alcohols having 6 to 12 carbon atoms, aliphatic and cycloaliphatic hydrocarbons, cycloaliphatic and aromatic aldehydes and ketones, N,N-dialkyl acetamides, aliphatic and cycloaliphatic esters, N,N-dialkyl sulfoxides, essential oils, nitrated aliphatic and cycloaliphatic hydrocarbons, salicylates, polyalkylene glycol silicates, aliphatic acids, terpenes, surfactants and siloxanes.

32. The process of claim 30, wherein said active agent enhancer comprises mineral oil.

33. The process of claim 1, wherein said active agent further comprises a liquid carrier compatible with said thermoplastic matrix polymer.

34. The process of claim 1, wherein said active ingredient melt-blended with said thermoplastic matrix polymer comprises said active agent enhancer, and said process further comprises the steps of:

(a) melt-blending a thermoplastic rate-controlling polymer capable of controllably releasing an active agent, with an active agent that is heat stable at the melt temperature of said rate-controlling polymer, so that a melt-blend of said active agent and said thermoplastic rate-controlling polymer is formed;

(b) forming said melt-blend of said active agent and said thermoplastic rate-controlling polymer into a rate-controlling polymer layer having an inner surface and an outer surface; and (c) laminating said inner surface of said rate-controlling polymer layer to said first surface of said carrier layer;

wherein said step of providing said laminate with means for securing said laminate to said skin or mucosa of said host comprises coating said outer surface of said rate-controlling polymer layer with an adhesive layer permeable to said active ingredient, so that said active agent enhancer is capable of being continuously released from said first surface of said carrier layer through said rate-controlling polymer layer and then released with said active agent from said outer surface of said rate-controlling polymer layer through said adhesive layer to said skin or mucosa of said host.

35. The process of claim 34, wherein said active agent comprises estradiol.

36. The process of claim 8, wherein said laminating step comprises affixing said rate-controlling polymer layer to said first surface of said carrier layer with an active ingredient permeable adhesive layer.

37. The process of claim 8, wherein said laminating step comprises extruding said rate-controlling polymer layer and said carrier layer together.

38. The process of claim 37, wherein said extruding step comprises coextruding said rate-controlling polymer layer and said carrier layer.

39. The process of claim 34, wherein said step of laminating said inner surface of said rate-controlling polymer layer to said first surface of said carrier layer comprises affixing said inner surface of said rate-controlling polymer layer to said first surface of said carrier layer with an adhesive layer permeable to said active agent enhancer.

40. The process of claim 34, wherein said step of laminating said rate-controlling polymer layer to said carrier layer comprises the step of extruding said rate-controlling polymer layer and said carrier layer together.

41. The process of claim 40, wherein said extruding step comprises coextruding said rate-controlling polymer layer and said carrier layer.

42. The process of claim 34, further comprising the step of melt-blending said rate-controlling polymer layer with said active agent enhancer to promote the penetration of said active agent through said skin or mucosa of said host, prior to laminating said rate-controlling polymer layer to said first surface of said carrier layer, so that a melt-blend of said active agent enhancer and said thermoplastic matrix polymer is formed.

43. The process of claim 34, further comprising the step of melt-blending said active agent permeable adhesive with said active agent enhancer to promote the penetration of said active agent through said skin or mucosa of said host, prior to coating said rate-controlling polymer layer on said surface opposite said carrier layer with said adhesive, so that a melt-blend of said active agent enhancer and said adhesive is formed.

44. The process of claim 1, wherein said extruding step comprises coextruding said backing layer and said carrier layer.

* * * * *

UNITED STATES PATENT AND TRADEMARK OFFICE
CERTIFICATE OF CORRECTION

PATENT NO. : 5,679,373
DATED : October 21, 1997
INVENTOR(S) : Wick et al.

It is certified that error appears in the above-identified patent and that said Letters Patent is hereby corrected as shown below:

Column 1, line 50, "stripped, substantially" should read --stripped substantially--.

Column 11, line 9, "layer" should read --layers--.

Column 12 line 9, "provide" should read --provided--.

Column 15, line 1, "FIG. I" should read --FIG. 1--.

Column 15, line 5, "questions" should read --question--.

Column 19 line 17, "both-" should read --both--.

Column 19 line 42, "if" should read --is--.

UNITED STATES PATENT AND TRADEMARK OFFICE
CERTIFICATE OF CORRECTION

PATENT NO. : 5,679,373
DATED : October 21, 1997
INVENTOR(S) : Wick et al.

It is certified that error appears in the above-identified patent and that said Letters Patent is hereby corrected as shown below:

Column 19 line 43, "occurs" should read --occurring--.

Column 20 line 33, "layer 22" should read --layer 222--.

Column 23 line 59, "and" should read --or--.

Column 23 line 66, "carrier" should read --carried--.

Column 31 line 48, "are" should read --is--.

Signed and Sealed this

Seventeenth Day of March, 1998

Attest:

BRUCE LEHMAN

*Attesting Officer*  *Commissioner of Patents and Trademarks*